(12) United States Patent
Neumann

(10) Patent No.: US 12,001,964 B2
(45) Date of Patent: Jun. 4, 2024

(54) ARTIFICIAL INTELLIGENCE ADVISORY SYSTEMS AND METHODS FOR BEHAVIORAL PATTERN MATCHING AND LANGUAGE GENERATION

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 18/115,831

(22) Filed: Mar. 1, 2023

(65) Prior Publication Data
US 2023/0206082 A1    Jun. 29, 2023

Related U.S. Application Data

(63) Continuation of application No. 16/502,819, filed on Jul. 3, 2019, now Pat. No. 11,625,615.

(51) Int. Cl.
| | | |
|---|---|---|
| G06F 16/00 | (2019.01) | |
| G06F 16/33 | (2019.01) | |
| G06N 5/02 | (2023.01) | |
| G06N 20/00 | (2019.01) | |

(52) U.S. Cl.
CPC ........... *G06N 5/02* (2013.01); *G06F 16/3344* (2019.01); *G06N 20/00* (2019.01)

(58) Field of Classification Search
CPC ...... G06N 5/02; G06N 20/00; G06F 16/3344; G06F 40/56

USPC .......................................................... 706/46
See application file for complete search history.

(56) References Cited

U.S. PATENT DOCUMENTS

| | | |
|---|---|---|
| 9,185,238 B1 | 11/2015 | Freeland et al. |
| 9,600,297 B1 | 3/2017 | Buyukkokten |
| 9,948,689 B2 | 4/2018 | Savage et al. |
| 9,965,553 B2 | 5/2018 | Lyren |
| 10,168,866 B2 | 1/2019 | Wakeen |
| 10,957,451 B2 * | 3/2021 | T .............................. G16H 50/50 |

(Continued)

OTHER PUBLICATIONS

Online spiritual advisor services; http://www.askforadvisors.com/psychic-readings/index.php; Apr. 22, 2019.

(Continued)

*Primary Examiner* — Monica M Pyo
(74) *Attorney, Agent, or Firm* — Caldwell Intellectual Property Law

(57) ABSTRACT

An artificial intelligence system for behavioral pattern matching and language generation includes at least a server. The system includes a behavior modification module operating on the at least a server, wherein the behavior modification module is designed and configured to receive at least a request for a behavior modification and generate a behavior modification model as a function of the at least a request for behavior modification. The system includes an artificial intelligence advisor operating on the at least a server, wherein the artificial intelligence advisor is configured to receive at least a user input from a user client device, generate at least a textual output using the behavior modification model and the at least a user input, and transmit the at least a textual output to the user client device.

20 Claims, 13 Drawing Sheets

(56) References Cited

U.S. PATENT DOCUMENTS

| | | |
|---|---|---|
| 11,074,994 B2* | 7/2021 | Pribanic .................. G06N 5/046 |
| 11,244,764 B2 | 2/2022 | Kailasam et al. |
| 2009/0048903 A1 | 2/2009 | Lieberman |
| 2014/0276244 A1 | 9/2014 | Kamyar |
| 2016/0162785 A1 | 6/2016 | Grobman |
| 2016/0212076 A1 | 7/2016 | Bellissimo et al. |
| 2016/0314265 A1 | 10/2016 | Sternberg et al. |
| 2017/0235849 A1 | 8/2017 | Jacob |
| 2018/0096740 A1* | 4/2018 | Moturu .................. G16H 15/00 |
| 2018/0206083 A1* | 7/2018 | Kumar .................... H04W 4/12 |
| 2019/0027052 A1 | 1/2019 | Moore |
| 2019/0066849 A1* | 2/2019 | Lawrence ............. G06F 40/205 |
| 2020/0320363 A1* | 10/2020 | Neumann ............... G06F 40/30 |
| 2021/0004377 A1* | 1/2021 | Neumann .............. G06Q 50/22 |
| 2021/0005316 A1* | 1/2021 | Neumann ................ G06N 3/08 |
| 2023/0223132 A1* | 7/2023 | Neumann ............. G06N 20/20 |
| | | 702/19 |

OTHER PUBLICATIONS

24 Astro Spiritual Advisor; https://play.google.com/store/apps/details?id=infrasat.astro24; Feb. 18, 2019.

Chatnow; https://chatnow.org/; Apr. 22, 2019.

\* cited by examiner

ARTIFICIAL INTELLIGENCE ADVISORY SYSTEMS AND METHODS FOR BEHAVIORAL PATTERN MATCHING AND LANGUAGE GENERATION

CROSS-REFERENCE TO RELATED APPLICATIONS

This application is a continuation of Non-provisional Application No. 16/502,819 filed on Jul. 03, 2019 and entitled "ARTIFICIAL INTELLIGENCE ADVISORY SYSTEMS AND METHODS FOR BEHAVIORAL PATTERN MATCHING AND LANGUAGE GENERATION," the entirety of which is incorporated herein by reference.

FIELD OF THE INVENTION

The present invention generally relates to the field of artificial intelligence. In particular, the present invention is directed to artificial intelligence advisory systems and methods for behavioral pattern matching and language generation.

BACKGROUND

Automated analysis of data and correct transmission of said data can be challenging due to the complexity of and multiplicity of data to be analyzed. Knowing which data should be transmitted to a user can be highly complex due to the unique and individual needs of each user—a problem exacerbated by the burgeoning volume of data available for analysis. Incorrect transmissions can lead to inaccuracies within systems, waste time trying to correct cumbersome issues, and ultimately frustrate users.

SUMMARY OF THE DISCLOSURE

In an aspect, an artificial intelligence system for behavioral pattern matching and language generation includes at least a server. The system includes a behavior modification module operating on the at least a server, wherein the behavior modification module is designed and configured to receive at least a request for a behavior modification and generate a behavior modification model as a function of the at least a request for behavior modification. The system includes an artificial intelligence advisor operating on the at least a server, wherein the artificial intelligence advisor is configured to receive at least a user input from a user client device, generate at least a textual output using the behavior modification model and the at least a user input, and transmit the at least a textual output to the user client device.

In another aspect an artificial intelligence method of behavioral pattern matching and language generation includes receiving, by at least a server, at least a request for a behavior modification. The method includes generating, by the at least a server, a behavior modification model as a function of the at least a request for behavior modification. The method includes receiving, by the at least a server, at least a user input from a user client device. The method includes generating, by the at least a server, at least a textual output using the behavior modification model and the at least a user input. The method includes transmitting, by the at least a server, the at least a textual output to the user client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Systems and methods are provided for machine-learning processing of heterogenous behavioral and linguistic datasets. In an embodiment, a behavioral modification module may classify user inputs to behavior modification data. Parsing and processing modules may receive textual inputs, which may be resolved to queries; queries may be converted to responses using language processing elements and/or retrieval of responses from informational resources. Informational resources may include a behavior modification module and/or behavior modification model. As a result, responses to queries based on complex user input data may be generated efficiently.

Figure 1:
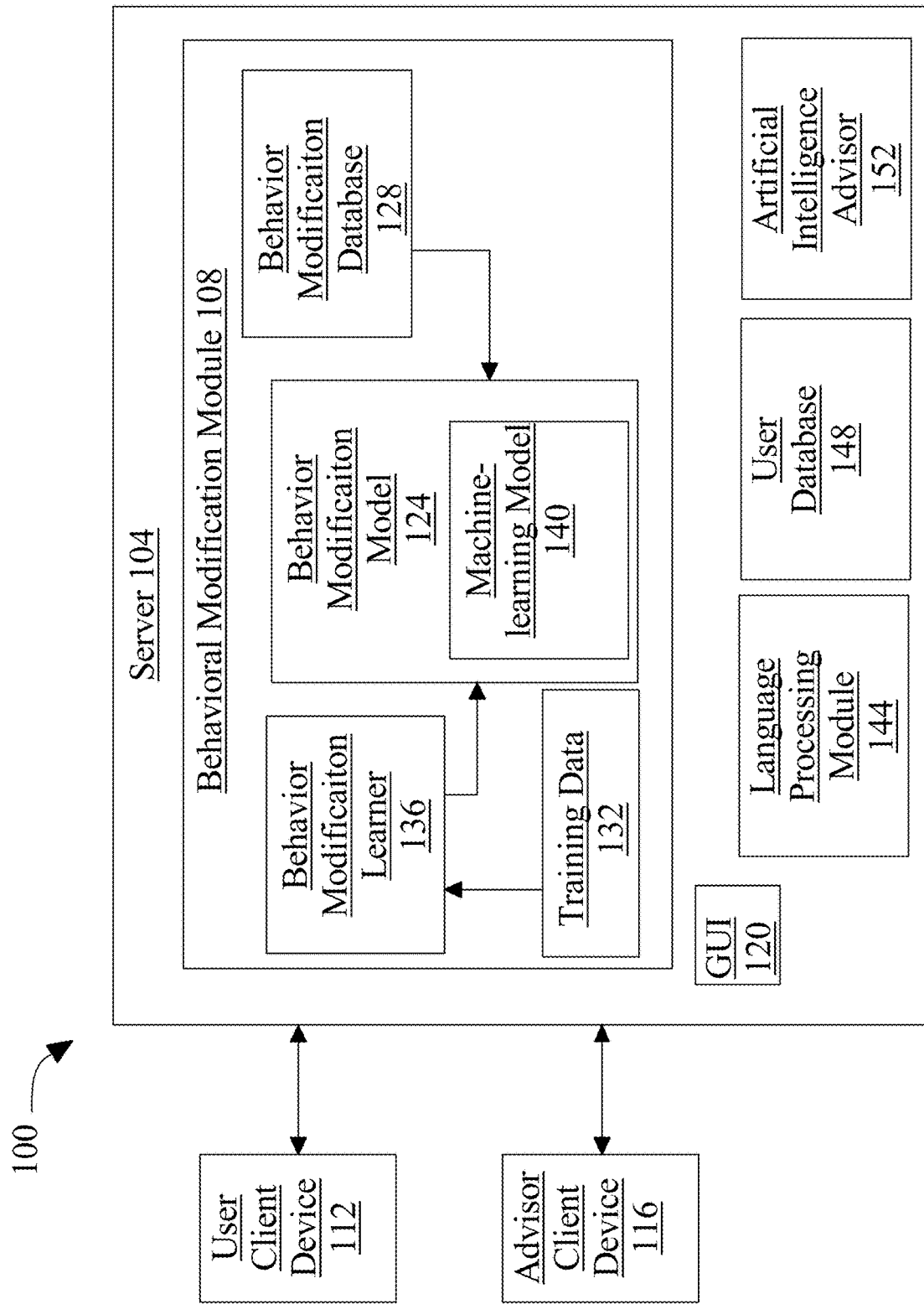
FIG. 1 is a block diagram of an exemplary embodiment of a system for behavioral pattern matching and language generation.

Turning now to FIG. 1, an artificial intelligence advisor 152 system 100 for vibrant constitutional guidance. Artificial intelligence advisor 152 system includes at least a server 104. At least a server 104 may include any computing device as described below in reference to FIG. 23, including without limitation a microcontroller, microprocessor, digital signal processor (DSP) and/or system on a chip (SoC) as described in this disclosure. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

Still referring to FIG. 1, at least a server 104 and/or one or more modules operating thereon may be designed and/or configured to perform any method, method step, or sequence of method steps in any embodiment described in this disclosure, in any order and with any degree of repetition. For instance, at least a server 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. Any module or modules introduced in this disclosure may be instantiated using any combination of software and/or hardware commands or circuitry as described in this disclosure, including without limitation logic circuits, software programs using functions, methods, and/or object-oriented programming, or the like. Although modules are introduced conceptually in the ensuing disclosure as separate components for the sake of clarity, persons skilled in the art, upon reviewing the entirety of this disclosure, will be aware that a module may be created, as contemplated in the scope of this disclosure, by any combination of circuitry and/or software program commands stored in any form; for instance, and without limitation, a module may not be identified within system 100 and/or at least a server 104 as a distinct entity or component, but may exist only as the combination of elements and/or commands performing the functions attributed herein to the module, and two or more modules may be partially or wholly combined together, may share functions, data, objects, and/or circuits.

Continuing to refer to FIG. 1, system 100 includes a behavior modification module 108 operating on the at least a server. Behavior modification module 108 may be implemented as any hardware module, software module, and/or combination thereof as described in this disclosure. Behavior modification module 108 is designed and configured to receive at least a request for a behavior modification. a "request for a behavior modification" as used herein is a request for a modification, which may be referred to in this disclosure as "behavior modification," to any action or response to a particular situation or stimulus. At least a request for a behavior modification may include for example, a request to stop a particular pattern of behavior or trait such as a desire to stop smoking, obtain more exercise, or quit drinking alcohol for example. At least a request for a behavior modification is utilized to extract at least a quality of an expert who may function to provide a user with encouragement, support, and advice to aid a user in overcoming a behavior modification. Different qualities may be desirable and/or undesirable for an expert as a function of the at least a request for a behavior modification. For example, a behavior modification such as drug addiction may be desirable to have an expert who is accountable and reliable but and not easily tempted by evil forces. User inputs and qualities may then be utilized to select an expert who may become part of a user's inner circle and aid a user in overcoming a particular behavior modification or allowing a behavior modification to enter a phase whereby it is maintained if it cannot be completely eliminated.

Still referring to FIG. 1, at least a request for behavior modification data may identify one or more problematic behaviors, the cessation of which the request for behavior modification identifies as a goal for a user; such problematic behaviors may include, without limitation, physical addictions to substances such as alcohol, tobacco, opioids, drugs, cocaine, cannabis, amphetamines, hallucinogens, inhalants, phencyclidine and the like. Problematic behaviors may include impulse control disorders such as intermittent explosive disorder, kleptomania, pyromania, gambling and the like. Problematic behaviors may include addictions to certain actions such as food, sex, pornography, computer use, device use such as cellphones, tablets, and the like; work, exercise, spiritual obsession, pain seeking, cutting, shopping and the like. Problematic behaviors may include modification to a trait one may exhibit in personal relationships at home, work, or school such as winning too much, passing judgment, making destructive comments, speaking when angry, extreme negativity, withholding information, making excuses, clinging to the past, playing favorites, failing to listen, failing to express gratitude, and the like. Problematic behaviors may include modification to thoughts, words, actions and deeds such as sexual immorality including impurity, orgies, and lust, idolatry including witchcraft, selfish ambition, demons, and demigods, debauchery including drunkenness, filthy language, and corruption, hatred including malice, deceit, and fits of rage, jealousy including envy, anger, greed and slander.

With continued reference to FIG. 1, behavior modification may include goal behaviors, such as a desire to lose weight, a desire to develop a spirituality practice, attend training sessions at a gym more frequently, develop a meditation practice, meet with a nutrition professional to discuss food plans and the like. Goal behaviors may include modification to a trait a user seeks to attain. For example, a goal behavior may include a desire to be driven by thoughts, words, actions and deeds surrounding traits such as love, joy, peace, patience, kindness, goodness, faithfulness, gentleness, and self-control. Goal behaviors may include, without limitation, behaviors demonstrating positive expert qualities as described in further detail below. Persons skilled in the art, upon reviewing the entirety of this disclosure, will be aware of various examples of goal behaviors consistently with this disclosure.

Still referring to FIG. 1, behavior modification may include one or more elements of user input data associated with problematic behaviors and/or goal behaviors. User input data may include any data that may be received from a user client device 112. User input data may include textual data, which may include without limitation strings of one or more characters, including without limitation any sequence or sequences of letters, numbers, punctuation, diacritic marks, engineering symbols, geometric dimensioning and tolerancin (GI)&T) symbols, chemical symbols and formulas, spaces, whitespace, and other symbols, including any symbols usable as textual data. as described above. Textual data may include one or more words, symbols and/or phrases associated with problematic and/or goal behaviors. For instance, and without limitation, a brand name or type of liquor may be associated with alcohol consumption, while various religious, supportive, and/or spiritual terms, including doctrines, pastoral titles, names of churches, addiction support groups, or the like may be associated with recovery from alcoholism, With continued reference to FIG. 1, user input data associated with behavior modification data, including without limitation problematic behavior and/or goal behavior, may include, without limitation, metadata. Meta.data may include, without limitation, a geographical location of a user client device 112, for instance as detected using navigational facilities and/or components such as the Global Positioning System (GPS). Metadata may include data usable for timestamps, including time of day, date, Julian date, or the like, as recorded using times and/or dates received over a network and/or one or more internal clocks and/or oscillators. Metadata may include a name or other identifying datum describing a person and/or device transmitting a message to a user client device 112. Metadata may include a name or other identifying datum describing a person and/or device to which a user client device 112 is transmitting. User input data may similarly include one or more images, videos, or other elements of data. Associations between user input data and problematic behaviors and/or goal behaviors may be established by correlation in data entries provided as part of behavior modification, such as entries by user and/or experts, advisors, and/or members of the user's support group indicating an association between the user input data and the problematic and/or goal behavior. Thus, as a non-limiting example, associations may be established according to recognition of such associations by user and/or other persons; as a result idiosyncratic metadata, images, terms and/or phrases associated with problematic and/or goal behaviors may be recorded as needed by system 100.

With continued reference to FIG. 1, system 100 may include a graphical user interface 120 (GUI) which may include without limitation a form or other graphical element having data entry fields, wherein one or more users, including without limitation user of user client device 112, advisors, supporters, and/or experts, may enter one or more elements of behavior modification as described above.. In an embodiment, fields in graphical user interface 120 may provide options describing previously identified elements of data, such as lists of common problematic and/or goal behaviors, problematic and/or goal behaviors concerning user of user client device 112, which may be retrieved from a user database 148 as described in further detail below lists of user input data elements commonly associated with one or more problematic and/or goal behaviors, or the like; for instance in "drop-down" lists, where users may be able to select one or more entries to indicate their associations as described above, in the opinion of the users. Fields may include free-form entry fields such as text-entry fields where an expert may be able to type or otherwise enter text, enabling entry of behavior modification data not currently recorded.

Still referring to FIG. 1, one or more elements of data as described above, and/or collections thereof, may be collected from and/or received from databases, previous iterations of methods or method steps as described herein, and/or input by one or more users. For instance, and without limitation, user input data and associated behavior modification data may be collected as training data and/or in databases as described in further detail below using instructions input by operators of system 100 and/or may be collected automatically during reception and/or processing of such data in the course of executing one or more method steps as described herein.

With continued reference to FIG. 1, at least a request for a behavior modification may be received from a user client device 112. A user client device 112 may include, without limitation, a display in communication with at least a server 104; display may include any display as described in this disclosure. A user client device 112 may include an additional computing device, such as a mobile device, laptop, desktop computer, or the like; as a non-limiting example, the user client device 112 may be a computer and/or workstation operated by a user. In an embodiment, a behavior modification received from a user client device 112 may be received from a user client device 112 operated by a user. For example, a user may generate a behavior modification that contains a request to quit drinking alcohol. In an embodiment, at least a request for a behavior modification may be received from a user client device 112 operated by a friend, family member, co-worker, and/or acquittance who may generate a request for a behavior modification from that person's own user client device 112 for the user. For example, a concerned family member of a user such as user's sister may generate at least a request for a behavior modification for user from sister's own user client device 112.

With continued reference to FIG. 1, at least a request for a behavior modification may be received from an advisor client device 116. Advisor client device 116 may include any device suitable for use as a user client device 112. In an embodiment, advisor client device 116 may be operated by an informed advisor. Informed advisor may include, without limitation, a medical professional such as a doctor, nurse, nurse practitioner, functional medicine practitioner, any professional with a career in medicine, nutrition, genetics, fitness, life sciences, spirituality, Christianity, insurance, and/or any other applicable industry that may contribute information and data to system 100 in regards to medical needs. An informed advisor may include for example, a spiritual or philosophical advisor such as a religious leader, a pastor, imam, rabbi, a religious teacher, or the like. For example, an informed advisor such as meditation teacher may generate at least a request for a behavior modification for a user such as one of the meditation teacher's students. In such an instance, the meditation teacher may generate the at least a request for a behavior modification for the teacher's student from advisor client device 116. In yet another non-limiting example, an informed advisor such as a functional medicine doctor may generate at least a request for a behavior modification from advisor client device 116 for a patient who self-reports to the functional medicine doctor an opioid addiction.

Still referring to FIG. 1, behavior modification module 108 is designed and configured to generate a behavior modification model 124 as a function of the at least a request for behavior modification. As used herein, a "behavior modification model 124" is a data structure, as instantiated using software logic, hardware logic, memory, or any combination thereof, that converts inputs made up of user input data as described above to outputs representing associated behaviors, which may include problematic behaviors and/or goal behaviors. Behavior modification model 124 may include one or more databases; for instance, and without limitation, behavior modification model 124 may include a behavior modification database 128. A behavior modification database 128 may include any data structure for ordered storage and retrieval of data, which may be implemented as a hardware or software module. A behavior modification database 128 may be implemented, without limitation, as a relational database, a key-value retrieval datastore such as a NOSQL database, or any other format or structure for use as a datastore that a person skilled in the art would recognize as suitable upon review of the entirety of this disclosure. A behavior modification database 128 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related behavior modification data. Data entries may include behavior modification data and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a behavior modification database 128 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a behavior modification database 128 may reflect categories, cohorts, and/or populations of data consistently with this disclosure.

Figure 2:
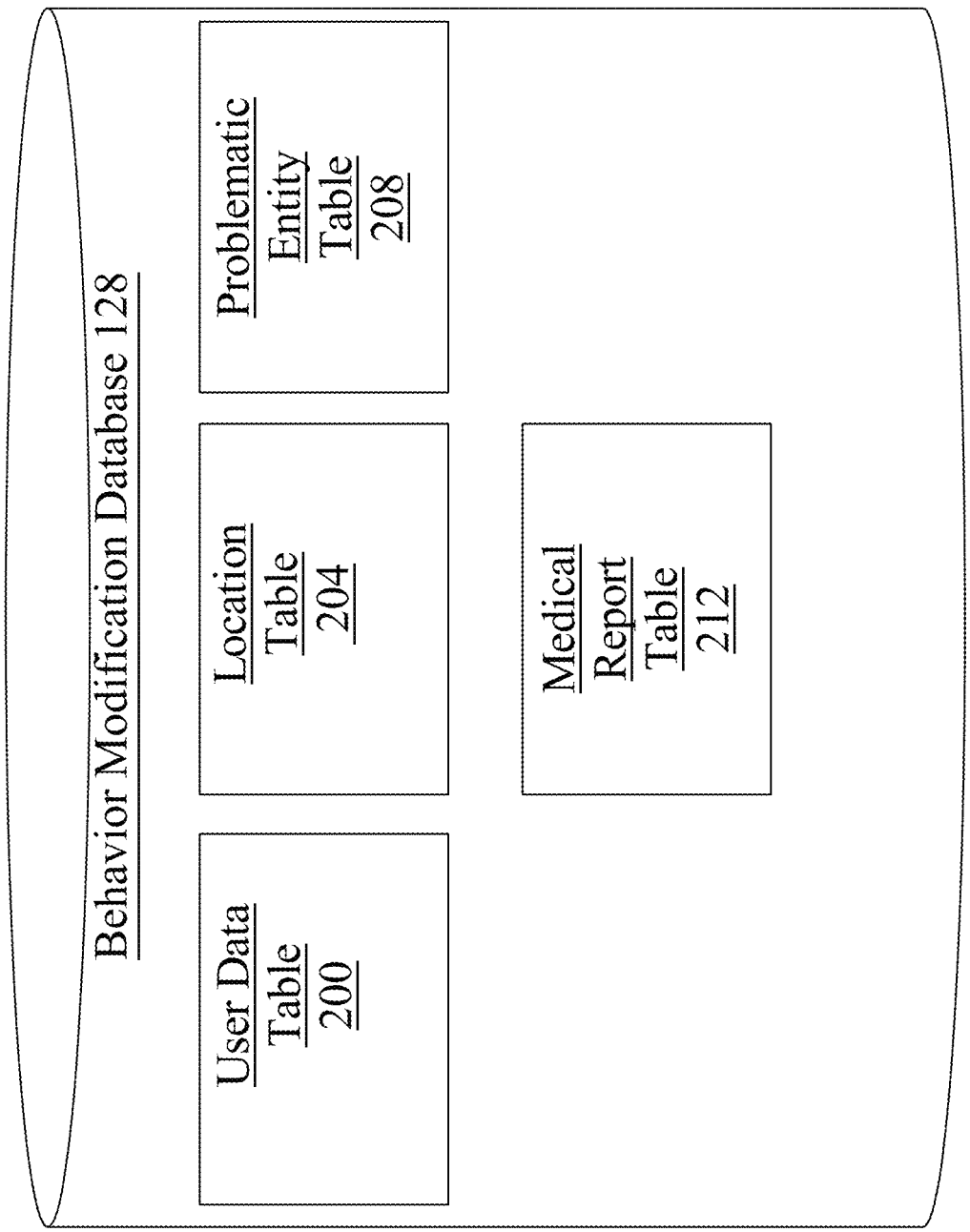
FIG. 2 is a block diagram illustrating an exemplary embodiment of a behavior modification database.

Referring now to FIG. 2, one or more database tables in behavior modification database 128 may include, as a non-limiting example, a user data table 200, which may list user information and/or link user identifying data to one or more other entries in behavior modification database 128. User data table 200 may alternatively or additionally provide identifying information to connect information from or in behavior modification database 128 with information from or in a user data table as described in further detail below. Behavior modification database 128 may include location table 204; location table may associate institutions, behaviors, persons, and/or substances with particular geographic locations. As a non-limiting example, a particular geographic location may be a location of a church, addiction support center, addiction treatment center, or a professional such as a psychologist, pastor, or the like who may be able to assist in encouraging goal behaviors and/or fighting against problematic behaviors; such associations may be listed in location table 204. As a further non-limiting example, a particular geographic location may be a location of a bar, a location frequented by a particular drug dealer, a location of a pornographic shop, a location of a brothel or prostitution-linked massage parlor, a house or office of a person or institution purveying products or services that encourage problematic behavior, or the like; such associations may be listed in location table 204 Behavior modification database 128 may include a problematic entity table 208; problematic entity table may list persons and/or establishments associated with problematic behaviors. Behavior modification database 128 may include a positive entity table 212, which may list persons and/or establishments associated with goal behaviors. Each of the above-described tables may have data linked to each other such table. Persons skilled in the art, upon reviewing the entirety of this disclosure, will be aware of various alternative or additional ways in which data may be organized in behavior modification database 128.

Referring again to FIG. 1, behavior modification model 124 may include and/or be generated using training data 132. Training data, as used herein, is data containing correlation that a machine-learning process may use to model relationships between two or more categories of data elements. For instance, and without limitation, training data 132 may include a plurality of data entries, each entry representing a set of data elements that were recorded, received, and/or generated together; data elements may be correlated by shared existence in a given data entry, by proximity in a given data entry, or the like. Multiple data entries in training data 132 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 132 according to various correlations; correlations may indicate causative and/or predictive links between categories of data elements, which may be modeled as relationships such as mathematical relationships by machine-learning processes as described in further detail below. Training data 132 may be formatted and/or organized by categories of data elements, for instance by associating data elements with one or more descriptors corresponding to categories of data elements. As a non-limiting example, training data 132 may include data entered in standardized forms by persons or processes, such that entry of a given data element in a given field in a form may be mapped to one or more descriptors of categories. Elements in training data 132 may be linked to descriptors of categories by tags, tokens, or other data elements; for instance, and without limitation, training data 132 may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data 132 may include one or more elements that are not categorized; that is, training data 132 may not be formatted or contain descriptors for some elements of data. Machine-learning algorithms and/or other processes may sort training data 132 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 132 to be made applicable for two or more distinct machine-learning algorithms as described in further detail below.

With continued reference to FIG. 1, training data 132 may relate user input data as defined above to behavior modification data, which may include without limitation data describing problematic behavior. For instance, training data 132 may include a plurality of data entries, each data entry including at least an element of behavior modification data and at least a correlated element of user input data. Behavior modification data may include data concerning problematic behaviors, such as data surrounding physical addictions to substances such as alcohol, tobacco, opioids, prescription drugs, cocaine, cannabis, amphetamines, hallucinogens, inhalants, phencyclidine and the like. Behavior modification data may include data concerning impulse control disorders such as intermittent explosive disorder, kleptomania, pyromania, gambling and the like. Behavior modification data may include data surrounding addictions to certain actions such as food, sex, pornography, computer use, device use such as cellphones, tablets, and the like; work, exercise, spiritual obsession, pain seeking, cutting, shopping and the like. Behavior modification data may include data concerning a trait one may exhibit in personal relationships at home, work, or school such as winning too much, passing judgment, making destructive comments, speaking when angry, extreme negativity, withholding information, making excuses, clinging to the past, playing favorites, failing to listen, failing to express gratitude, and the like. Behavior modification data may include data associated with behaviors including thoughts, words, actions and deeds such as sexual immorality including impurity, orgies, and lust, idolatry including witchcraft, selfish ambition, demons, and demigods, debauchery including drunkenness, filthy language, and corruption, hatred including malice, deceit, and fits of rage, jealousy including envy, anger, greed and slander and/or perceptions thereof. Behavior modification data may include data describing a trait a user may exhibit surrounding one's lifestyle such as a desire to lose weight, a desire to develop a spirituality practice, attend training sessions at a gym more frequently, develop a meditation practice, meet with a nutrition professional to discuss meal plans and the like. Behavior modification may include data describing and/or associated with one or more goal behaviors, including without limitation data describing and/or indicating a trait a user seeks to attain as described above. Correlated user input data may include any user input data included in a data entry with a correlated element of behavior modification data; inclusion together may be performed based on entries received that include the behavior modification data and the user input data together, such as a user entry indicating that a given word or phrase, element of metadata, image, or the like is associated with a given element of behavior modification data, as described above.

In an embodiment, and with continued reference to FIG. 1, behavior modification module 108 may include a behavior modification learner 136, which may generate behavior modification model 124 using one or more methods of machine learning as a function of a user inputs and/or training data 132. A "machine learning" process as used in this disclosure is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, behavior modification learner 136 may be designed and configured to generate behavior modification data by creating at least a machine-learning model 140 relating user input data to behavior modification data using the training data 132 and generating the behavior modification data using the machine learning model; at least a machine-learning model 140 may include one or more models that determine a mathematical relationship between user input data and behavior modification data. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Machine-learning may include other regression algorithms, including without limitation polynomial regression.

Continuing to refer to FIG. 1, machine-learning algorithm used to generate machine learning model may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, behavior modification learner 136 may output behavior modification data based on user inputs using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data the trained network may then be used to apply detected relationships between elements of user input data and behavior modification data.

Figure 3:
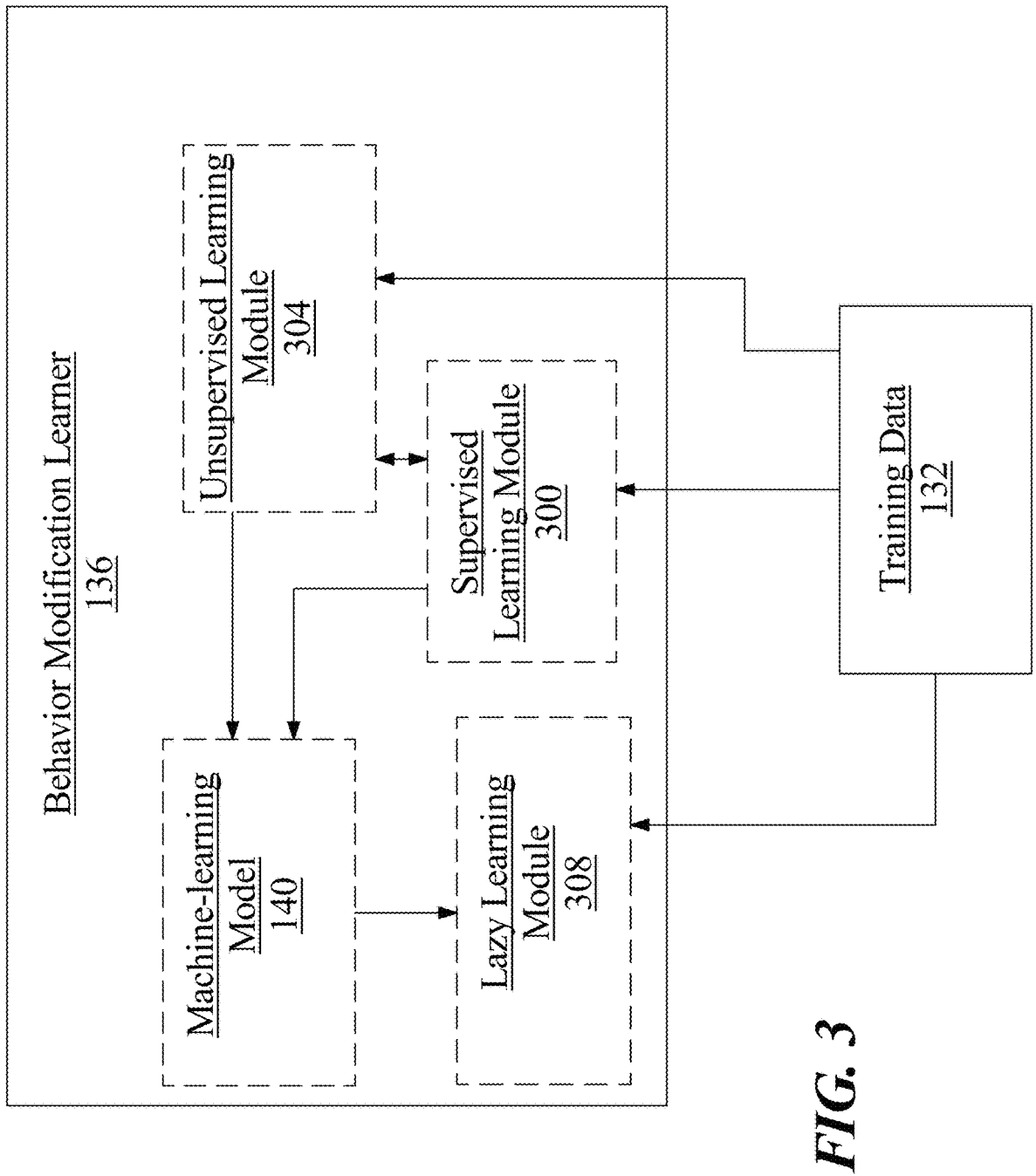
FIG. 3 is a block diagram illustrating an exemplary embodiment of a behavior modification learner.

Referring now to FIG. 3, machine-learning algorithms used by behavior modification learner 136 may include supervised machine-learning algorithms, which may, as a non-limiting example be executed using a supervised learning module 300 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of user input data as inputs, behavior modification data as outputs, and a scoring function representing a desired form of relationship to be detected between elements of user input data and behavior modification data; scoring function may, for instance, seek to maximize the probability that a given element of user input data and/or combination of elements of user input data is associated with a given element of behavior modification data and/or combination of behavior modification data to minimize the probability that a given element of user input data and/or combination of elements of user input data is not associated with a given element of behavior modification data and/or combination of behavior modification data. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 132. Persons skilled in the art, upon reviewing the entirety of this disclosure, will be aware of various possible variations of supervised machine learning algorithms that may be used to determine relation between elements of user input data and behavior modification data. In an embodiment, one or more supervised machine-learning algorithms may be restricted to a particular domain; for instance, a supervised machine-learning process may be performed with respect to a given set of parameters and/or categories of parameters that have been suspected to be related to a given set of behavior modification data, and/or are specified as linked to a category of behavior modification data. Domain restrictions may be suggested by experts and/or deduced from known purposes for particular evaluations and/or known user data associated with behavior modification data. Additional supervised learning processes may be performed without domain restrictions to detect, for instance, previously unknown and/or unsuspected relationships between user input data and behavior modification data. Domain restrictions may include, as a non-limiting example, limitation to a particular user operating a particular user client device 112; as a result, at least machine-learning model 140 specific to a user may be generated, which may learn associations unique to that user.

Still referring to FIG. 3, machine-learning algorithms may include unsupervised processes; unsupervised processes may, as a non-limiting example, be executed by an unsupervised learning module 304 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, behavior modification learner 136 and/or at least a server 104 may perform an unsupervised machine learning process on training data 132, which may cluster data of training data 132 according to detected relationships between elements of the training data 132, including without limitation correlations of elements of user input data to each other and correlations of behavior modification data to each other; such relations may then be combined with supervised machine learning results to add new criteria for behavior modification learner 136 to apply in relating user input data to behavior modification data. As a non-limiting, illustrative example, an unsupervised process may determine that a first element of user input data correlates closely with a second element of user input data, where the first element has been linked via supervised learning processes to a given behavior modification datum, but the second has not; for instance, the second element may not have been defined as an input for the supervised learning process, or may pertain to a domain outside of a domain limitation for the supervised learning process. As noted above, domain restrictions may include, as a non-limiting example, limitation to a particular user operating a particular user client device 112; as a result, at least machine-learning model 140 specific to a user may be generated, which may learn associations unique to that user. Continuing the example a close correlation between first element of user input data and second element of user input data may indicate that the second element is also a good predictor for the behavior modification data; second element may be included in a new supervised process to derive a relationship or may be used as a synonym or proxy for the user input data by behavior modification learner 136.

Still referring to FIG. 1, at least a server 104 and/or behavior modification learner 136 may detect further significant categories of user input data, relationships of such categories to behavior modification data, and/or categories of behavior modification data using machine-learning processes, including without limitation unsupervised machine-learning processes as described above; such newly identified categories, as well as categories entered by users in free-form fields as described above, may be added to pre-populated lists of categories, lists used to identify language elements for language learning module, and/or lists used to identify and/or score categories detected in documents, as described above. In an embodiment, as additional data is added to system 100, behavior modification learner 136 and/or at least a server 104 may continuously or iteratively perform unsupervised machine-learning processes to detect relationships between different elements of the added and/or overall data; in an embodiment, this may enable system 100 to use detected relationships to discover new correlations between known user input data, and behavior modification data, and one or more elements of data in large bodies of data. Use of unsupervised learning may greatly enhance the accuracy and detail with which system may detect behavior modification data.

With continued reference to FIG. 1, unsupervised processes may be subjected to domain limitations. For instance, and without limitation, an unsupervised process may be performed regarding a comprehensive set of data regarding one person. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of user input data, a group of people having a shared value for an element and/or category of behavior modification data. Persons skilled in the art, upon reviewing the entirety of this disclosure, will be aware of a multiplicity of ways in which cohorts and/or other sets of data may be defined and/or limited for a particular unsupervised learning process.

Still referring to FIG. 3, behavior modification learner 136 may alternatively or additionally be designed and configured to generate behavior modification data by executing a lazy learning process as a function of the training data 132 and the user input data; lazy learning processes may be performed by a lazy learning module 308 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at behavior modification data associated with user input data, using training data 132. As a non-limiting example, an initial heuristic may include a ranking of behavior modification data according to relation to a test type of at least a user input data, one or more categories of user input data, and/or one or more values detected in user input data. Heuristic may include selecting some number of highest-ranking associations and/or behavior modification data. Behavior modification learner 136 may alternatively or additionally implement any suitable "lazy learning" algorithm, including without limitation a K-nearest neighbors algorithm, a lazy naive Bayes algorithm, or the like; persons skilled in the art, upon reviewing the entirety of this disclosure, will be aware of various lazy-learning algorithms that may be applied to generate behavior modification data as described in this disclosure, including without limitation lazy learning applications of machine-learning algorithms as described in further detail below. Training data 132 used by lazy learning module 308 may be limited by domain restrictions. Domain restrictions may include, as a non-limiting example, limitation to a particular user operating a particular user client device 112; as a result, outputs specific to a user may be generated, which may reflect associations unique to that user.

Referring again to FIG. 1, at least a server 104 may include a language processing module 144 designed and configured to parse the at least a textual submission and extract the at least a diagnostic constraint. Language processing module 144 may include any hardware and/or software module. Language processing module 144 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 144 may compare extracted words to user input data and/or behavior modification data, or the like. In an embodiment, one or more words and/or phrases may be enumerated, to find total count of mentions in textual data. Alternatively or additionally, language processing module 144 may operate to produce a language processing model. Language processing model may include a program automatically generated by at least a server 104 and/or language processing module 144 to produce associations between one or more words extracted from at least a document and detect associations, including without limitation mathematical associations, between such words, and/or associations of extracted words with user input data and/or behavior modification data. Associations between language elements, where language elements include for purposes herein extracted words, user input data and/or behavior modification data. may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given user input datum and/or behavior modification datum. As a further example, statistical correlations and/or mathematical associations may include probabilistic formulas or relationships indicating a positive and/or negative association between at least an extracted word and a user input datum and/or behavior modification datum; positive or negative indication may include an indication that a given document is or is not indicating a user input datum and/or behavior modification datum is or is not associated with a given word. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at least a server 104, or the like.

Still referring to FIG. 1, language processing module 144 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HM Ms as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 144 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 144 may use a corpus of documents to generate associations between language elements in a language processing module 144, and at least a server 104 may then use such associations to analyze words extracted from one or more documents and determine that the one or more documents indicate significance of an association between at least an extracted word and user input data and/or behavior modification data. In an embodiment, at least a server 104 may perform this analysis using a selected set of significant documents, such as documents identified by one or more experts as representing good science, good clinical analysis, or the like; an expert or experts may identify or enter such documents via graphical user interface 120 as described in further detail below, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, at least a server and/or behavior modification module 108 may use language processing module 144 to match one or more words and/or phrases entered as described above with related words and/or phrases. For instance two or more words or phrases, while not identical, may have highly similar semantic meaning, which may be reflected in higher degrees of proximity in a language model, such as vectors having a high degree of cosine similarity in a vector space as described above. In an embodiment, this may be used to standardize training sets, for instance by substituting synonymous terms and/or phrases with a "canonical" term or phrase, such that statistical enumeration of relationships may be made accurately.

In an embodiment, and still referring to FIG. 1, behavior modification model 124 may include and/or be included in a user database 148 in which data concerning a user of user client device 112 may be stored. User database 148 may include any structure and/or component suitable for use as behavior modification database 128 as described above.

Figure 4:
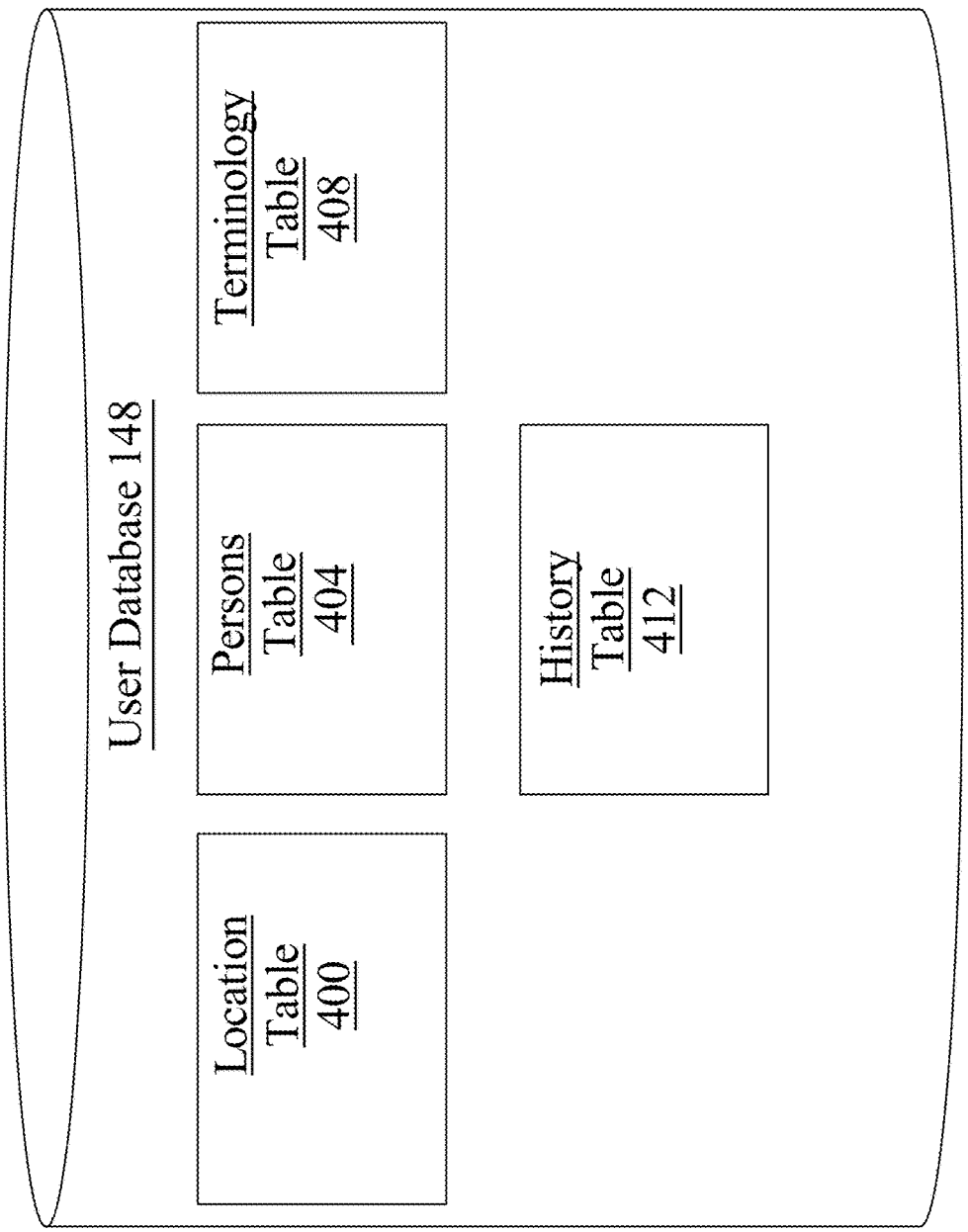
FIG. 4 is a block diagram illustrating an exemplary embodiment of a user database.

Referring now to FIG. 4, an exemplary embodiment of user database 148 is illustrated. One or more database tables in user database 148 may include, without limitation, a user category table; user category table may include information pertaining to a user's preference for a particular category of expert. For example, a user with a behavior modification such as weight loss may have a preference for an expert such as a nutritionist or dietician. One or more database tables in user database 148 may include, without limitation, a location table 400; location table 400 may include information pertaining to a user's interactions with one or more locations, including problematic and/or goal behaviors performed or intended to be performed at the location. One or more database tables in user database 148 may include, without limitation, a person table 404; person table 404 may include information pertaining to a user's interactions with one or more persons, including persons associated with problematic and/or goal behaviors. One or more database tables in user database 148 may include, without limitation, a terminology table 408; terminology table 408 may include data connecting one or more terms or phrases used by user and/or people known to user with other data, such as without limitation data in behavior modification database 128, training data 132 and/or other tables of user database 200. One or more database tables in user database 148 may include, without limitation, a history table 412; history table 412 may include describing a user's history of actions and/or interactions, including without limitation history of problematic behaviors, requests for behavior modification, and/or actions engaged in for behavior modification.

Referring again to FIG. 1, system 100 includes an artificial intelligence advisor 152 operating on the at least a server. Artificial intelligence advisor 152 may include any software module, hardware module, or combination thereof, as described in this disclosure. Artificial intelligence advisor 152 is configured to receive at least a user input from a user client device 112. At least a user input may be entered by the user in any suitable way, including without limitation by typing a textual input, providing a voice input, which may be converted to textual data via a voice-to-text program, or the like; at least a user input may be provided via a graphical user interface 120 as described above.

With continued reference to FIG. 1, artificial intelligence advisor 152 is configured to perform a user textual conversation with the user client device 112 by generating at least a textual output using the behavior modification model 124 and the at least a user input and transmitting the at least a textual output to the user client device 112. Inputs and/or outputs may be exchanged using messaging services and/or protocols, including without limitation any instant messaging protocols. Persons skilled in the art, up reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms. Artificial intelligence advisor 152 is configured to generate at least a textual output using diagnostic output and at least a user input, as set forth in further detail below.

Figure 5:
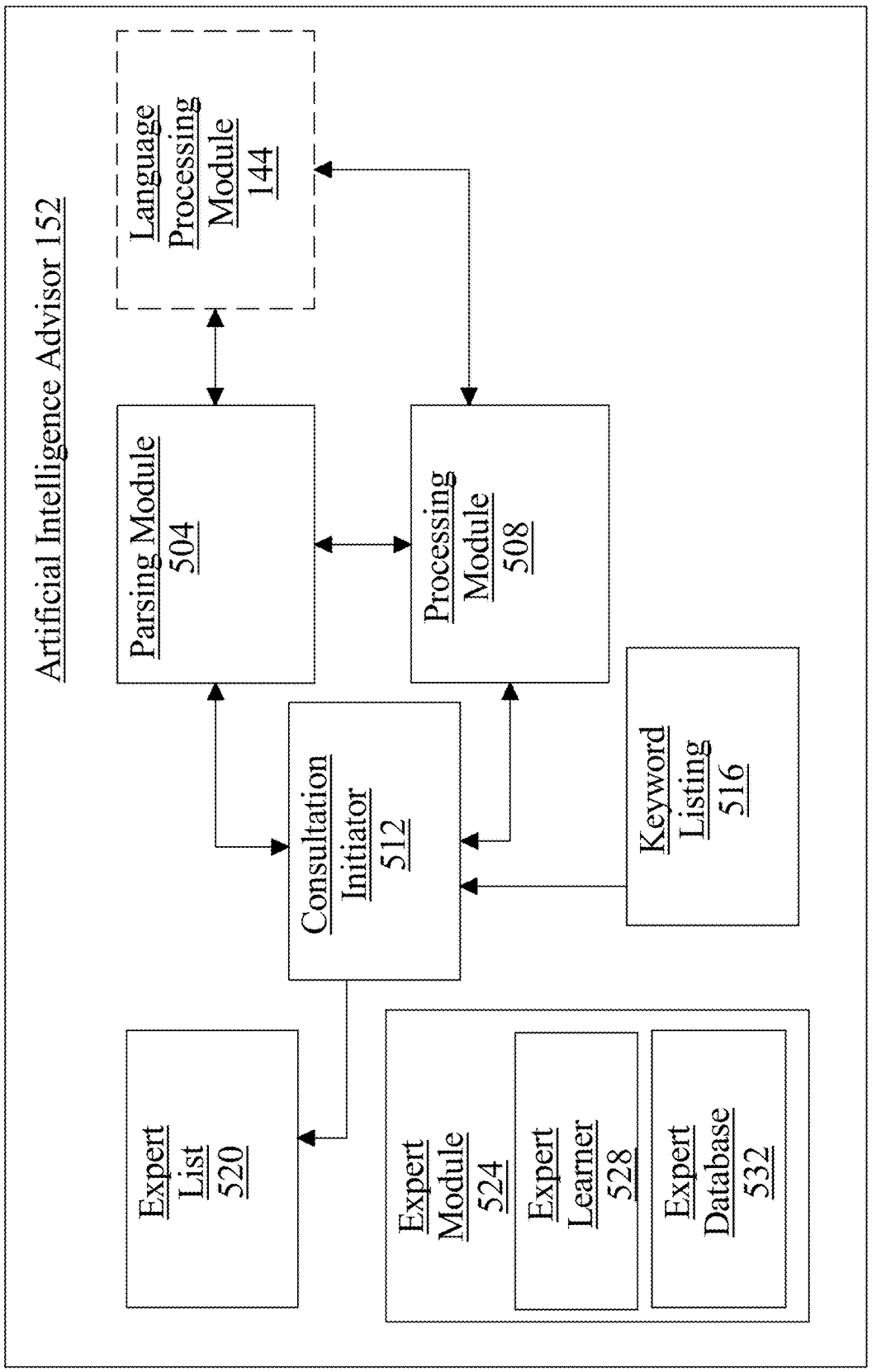
FIG. 5 is a block diagram illustrating an exemplary embodiment of an artificial intelligence advisor.

Referring now to FIG. 5, an exemplary embodiment of an artificial intelligence advisor 152 is illustrated. In an embodiment, artificial intelligence advisor 152 includes a parsing module 504 configured to generate at least a query using the at least a user input. At least a query, as used in this disclosure, is at least a datum used to retrieve text that will be incorporated in at least a textual output, where retrieval may be effected by inputting the at least a query into a data structure, database, and/or model, and receiving a corresponding output as a result, for example as set forth in further detail below. Parsing module 504 may generate at least a query by extracting one or more words or phrases from the input, where the input includes textual data, and/or analyzing one or more words or phrases; extraction and/or analysis may include tokenization, for instance as described above in relation to language processing module 144. In an embodiment, parsing module 504 may utilize, incorporate, or be a language processing module 144 as described above. Language processing module 144 may be configured to map at least a user input to at least a query, using any process as described above for a language processing module 144. Extraction and/or analysis may further involve polarity classification, in which parsing module 504 may determine, for instance, whether a phrase or sentence is a negation of the semantic content thereof, or a positive recitation of the semantic content. Polarity classification may be performed, without limitation, by consultation of a database of words that negate sentences, and/or geometrically within a vector space, where a negation of a given phrase may be distant from the non-negated version of the same phrase according to norms such as cosine similarity.

Still referring to FIG. 5, where user input includes textual data, parsing module 504 may be configured to normalize one or more words or phrases of user input, where normalization signifies a process whereby one or more words or phrases are modified to match corrected or canonical forms; for instance, misspelled words may be modified to correctly spelled versions, words with alternative spellings may be converted to spellings adhering to a selected standard, such as American or British spellings, capitalizations and apostrophes may be corrected, and the like; this may be performed by reference to one or more "dictionary" data structures listing correct spellings and/or common misspellings and/or alternative spellings, or the like. Parsing module 504 may perform algorithms for named entity recognition. Named entity recognition may include a process whereby names of users, names of informed advisors such as doctors, medical professionals, coaches, trainers, family members or the like, addresses, place names, entity names, or the like are identified; this may be performed, without limitation, by searching for words and/or phrases in user database 148. For instance, parsing module 504 may identify at least a phrase, which may include one or more words, map the at least a phrase to at least a query element, and then assemble a query using the at least a query element. Mapping at least a phrase to at least a query element may be performed using any language processing technique described in this disclosure, including vector similarity techniques.

With continued reference to FIG. 5, parsing module 504 may extract and/or analyze one or more words or phrases by performing dependency parsing processes; a dependency parsing process may be a process whereby parsing module 504 and/or a language processing module 144 communicating with and/or incorporated in parsing module 504 recognizes a sentence or clause and assigns a syntactic structure to the sentence or clause. Dependency parsing may include searching for or detecting syntactic elements such as subjects, objects, predicates or other verb-based syntactic structures, common phrases, nouns, adverbs, adjectives, and the like; such detected syntactic structures may be related to each other using a data structure and/or arrangement of data corresponding, as a non-limiting example, to a sentence diagram, parse tree, or similar representation of syntactic structure. Parsing module 504 may be configured, as part of dependency parsing, to generate a plurality of representations of syntactic structure, such as a plurality of parse trees, and select a correct representation from the plurality; this may be performed, without limitation, by use of syntactic disambiguation parsing algorithms such as, without limitation, Cocke-Kasaini-Younger (CKY), Earley algorithm or Chart parsing algorithms. Disambiguation may alternatively or additionally be performed by comparison to representations of syntactic structures of similar phrases as detected using vector similarity, by reference to machine-learning algorithms and/or modules such as without limitation a user communication learner as described below, or the like.

Continuing to refer to FIG. 5, parsing module 504 may analyze and/or create a query based on one or more elements metadata as described above. One or more elements of metadata may be provided to parsing module 504 in numerical and/or textual form; parsing module 504 may flag and/or mark one or more elements of metadata to indicate a category to which the one or more elements of metadata belong. For instance, metadata may be flagged to identify it as location data such as GPS or map coordinates, as time-identifying data such as timestamps, or the like. Language processing, database, and/or machine-learning processes and/or components, as well as parsing module 504, may process and/or identify associations between metadata and behavior modification data in the same way as for other textual data. Persons skilled in the art, upon reviewing the entirety of this disclosure, will be aware of various ways in which metadata may be processed and/or used as part of any process or processes as described herein.

Still referring to FIG. 5, parsing module 504 may combine separately analyzed elements from at least a user input together to form a single query; elements may include words, phrases, sentences, or the like, as described above. For instance, two elements may have closely related meanings as detected using vector similarity or the like; as a further non-limiting example, a first element may be determined to modify and/or have a syntactic dependency on a second element, using dependency analysis or similar processes as described above. Combination into a query may include, without limitation, concatenation. Alternatively or additionally, parsing module 504 may detect two or more queries in a single user input of at least a user input; for instance, parsing module 504 may extract a conversational query and an informational query from a single user input. An informational query, as used in this disclosure, is a query used to retrieve one or more elements of factual information; one or more elements may include, without limitation, any data suitable for use as behavioral modification data, and/or user input data as described above. One or more elements may include an identity of any factual element, including an identity of a place, person, user, entity, or the like. A conversational query, as used herein, is a query used to generate a textual response and/or response form, such as an overall sentence structure, templates, words, and/or phrases such as those usable for entries in default response database as described herein, for inclusion of information returned in response to an informational query, for a response to a question, comment, phrase, or sentence that is not in itself a request for information, and/or for a request for clarification and/or more information as described in further detail below. A conversational query may include one or more pattern-matching elements, such as regular expressions, "wildcards," or the like.

With continued reference to FIG. 5, parsing module 504 may be configured to convert at least a query into at least a canonical or standard form of query; for instance, and without limitation, once a query has been detected, parsing module 504 may convert it to a highly closely related query based on vector similarity, where the highly closely related query is labeled as a standard form or canonical query. In an embodiment, converting to a standard form query may enable more efficient processing of queries as described below, as a reduced space of potential queries may be used to retrieve conversational and/or informational responses. This may be accomplished using language processing module 144 and/or models or data structures created thereby, such as without limitation vector spaces.

Figure 6:
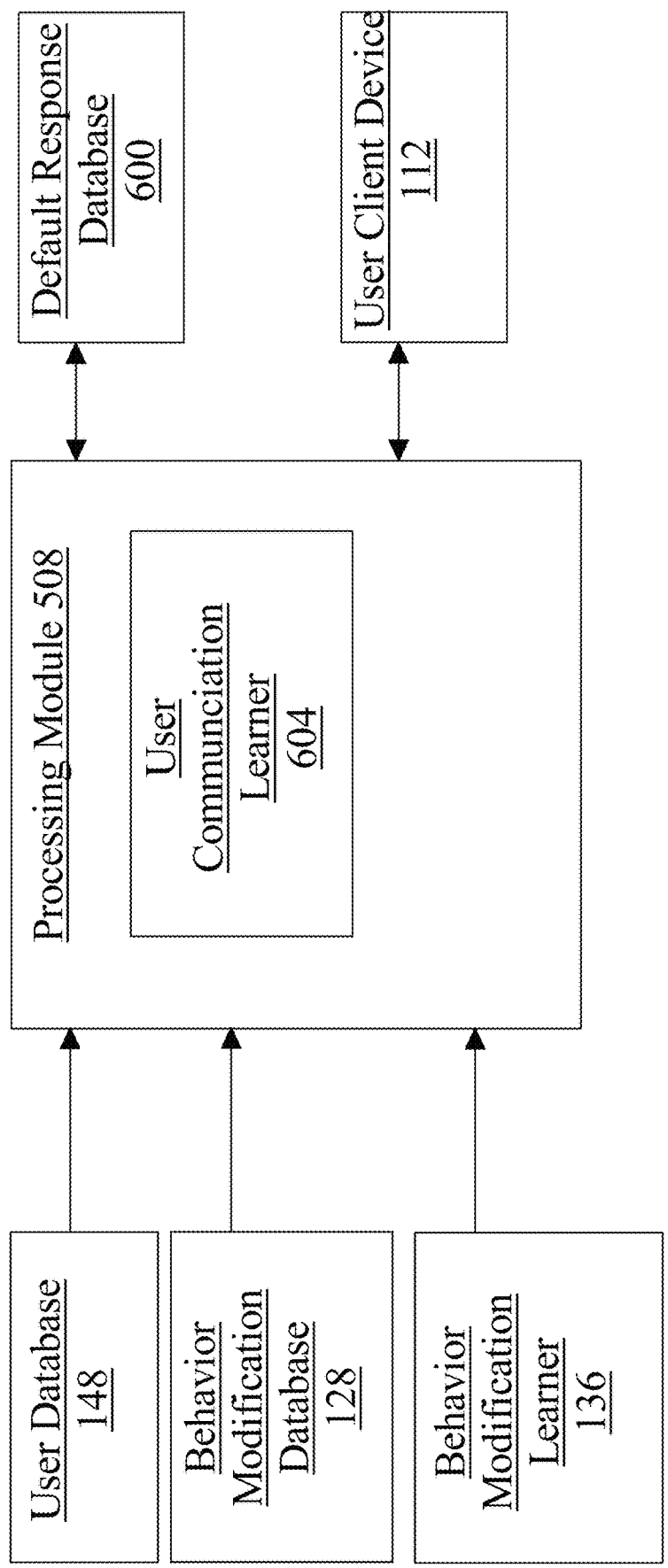
FIG. 6 is a block diagram illustrating an exemplary embodiment of a processing module.

Continuing to refer to FIG. 5, artificial intelligence advisor 152 may include a processing module 508 configured to generate the at least a textual output as a function of the at least a query. Referring now to FIG. 6, an exemplary embodiment of a processing module 508 is illustrated. In an embodiment, processing module 508 may be configured to determine that the at least a query includes a conversational language query and generate a conversational response using the conversational language query. In an embodiment, and as a non-limiting example, processing module 508 may be configured to generate the conversational response by retrieving at least a datum from a conversational resource, which for purposes of this disclosure is a data structure, database, data store, and/or data module that returns data usable to generate a conversational response when queried using a conversational language query. A conversational resource may include a default response database 600; for instance, processing module 508 may be configured to retrieve at least a datum from a default response database 600 using a conversational language query, and generate the conversational response using the at least a datum. Default response database 600 may link inputs to outputs according to initial relationships entered by users, including without limitation experts as described above, and/or as created by a previous instance or version of general learner and/or user-specific learner. Default response database 600 may periodically be updated with information from newly generated instances machine-learning models 140 and/or modules, or other components of artificial intelligence advisor 152. Inputs received by artificial intelligence advisor 152 may be mapped to canonical and/or representative inputs by synonym detection as performed, for instance, by a language processing module 144; language processing module 144 may be involved in textual analysis and/or generation of text at any other point in machine-learning and/or communication processes undergone by artificial intelligence advisor 152.

Figure 7:
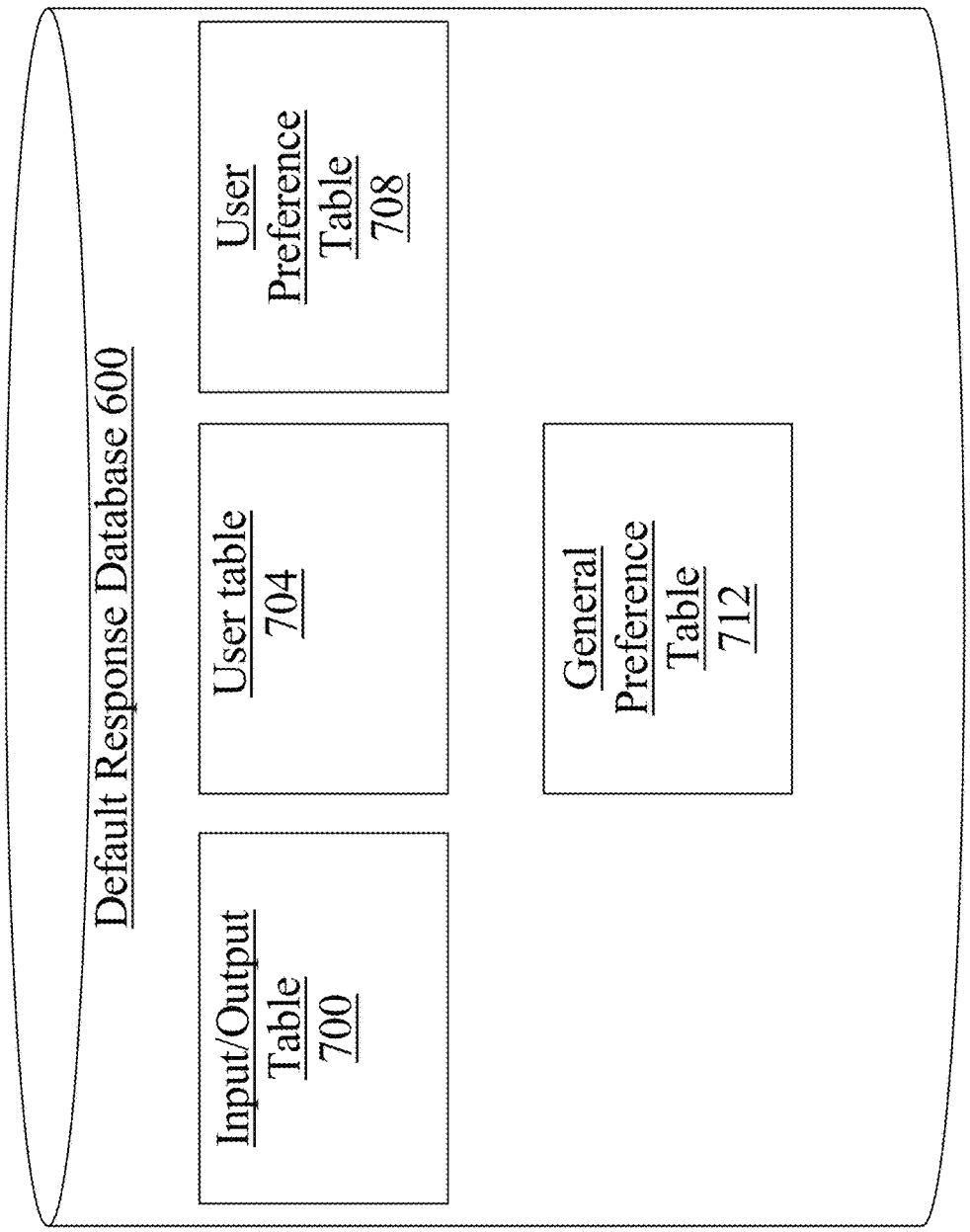
FIG. 7 is a block diagram illustrating an exemplary embodiment of a default response database.

Referring now to FIG. 7, an exemplary embodiment of a default response database 600 is illustrated. Default response database 600 may be implemented as any database and/or datastore suitable for use as behavioral modification database as described above. One or more database tables in default response database 600 may include, without limitation, an input/output table 700, which may link default inputs to default outputs. Default response database 600 may include a user table 704, which may, for instance, map users and/or a user client device 112 to particular user-specific learners and/or past conversations. Default response database 600 may include a user preference table 708 listing preferred modes of address, turns of phrase, or other user-specific communication preferences. Default response database 600 may include a general preference table 712, which may track, for instance, output-input pairings associated with greater degrees of user satisfaction. Where multiple records and/or responses may be retrieved from default response database 600, processing module 508 may relate such records hierarchically, for instance using hierarchical pattern-matching programs.

Figure 8:
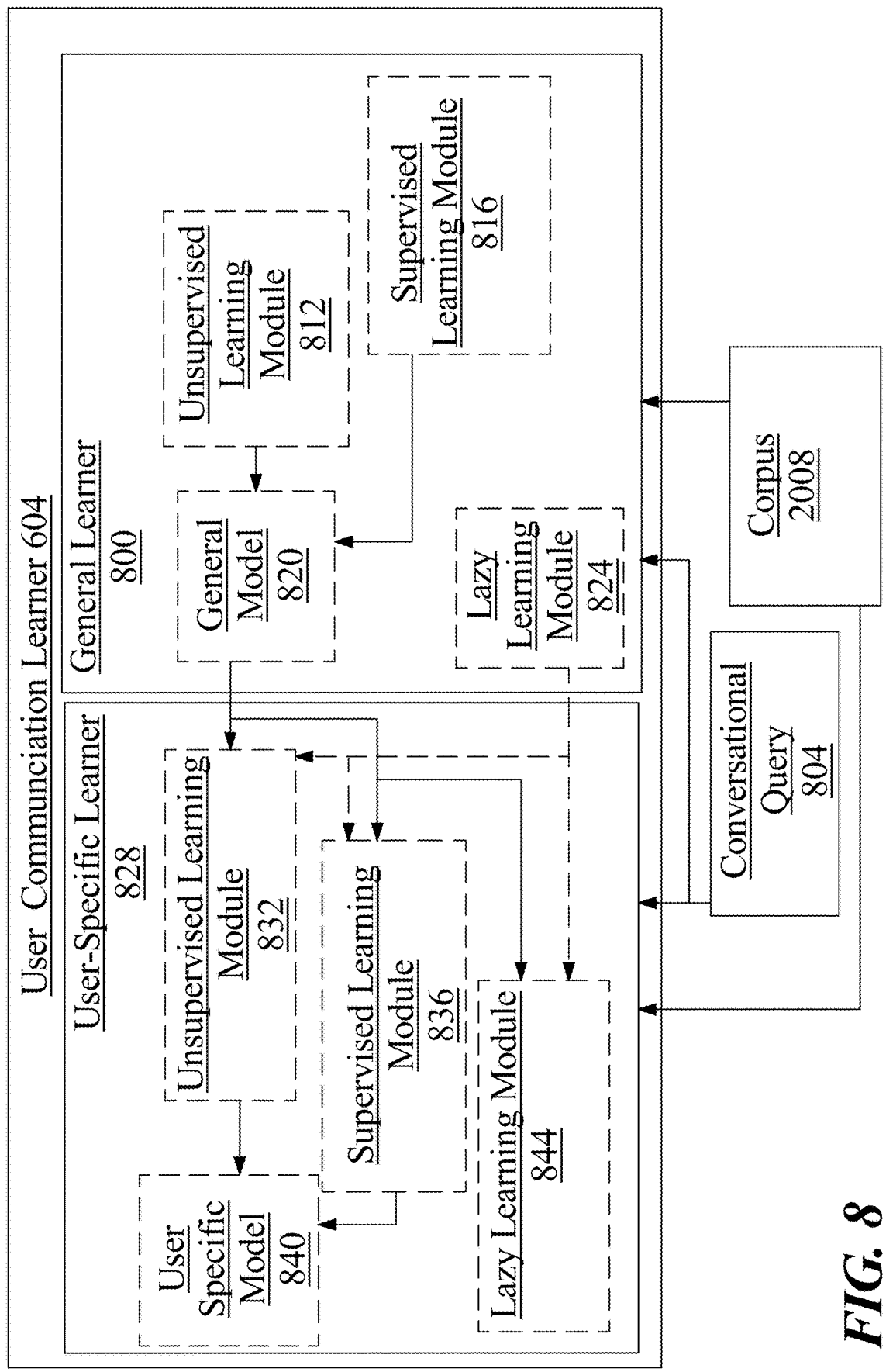
FIG. 8 is a block diagram illustrating an exemplary embodiment of a user communication learner.

Referring again to FIG. 6, processing module 508 and/or a conversational resource may include a user communication learner 604 configured to generate the at least a conversational response using the conversational language query. Referring now to FIG. 8, an exemplary embodiment of a user communication learner 604 is illustrated. User communication learner 604 may include any form of machine-learning learner as described above, implementing any form of language processing and/or machine learning. In an embodiment, user communication learner 604 may include a general learner 800; general learner 800 may be a learner that derives relationships between a conversational query 804 and correct outputs using a training set that includes, without limitation, a corpus 808 of previous conversations. Corpus 808 of previous conversations may be logged by at least a server 104 as conversations take place; user feedback, and/or one or more functions indicating degree of success of a conversation may be used to differentiate between positive input-output pairs to use for training and negative input-output pairs not to use for training.

Outputs may include textual strings and/or outputs from any databases, modules, and/or learners as described in this disclosure, including without limitation behavior modification data, user input data, user information, or the like; for instance, general learner may determine that some inputs optimally map to textual response outputs, while other inputs map to outputs created by retrieval of module and/or database outputs, such as retrieval of behavioral modification data, user input data, or the like. General learner 800 may include any elements suitable for use in any machine-learning module and/or learner as described in this description, including without limitation an unsupervised learning module 812 and/or a supervised learning module 816. General learner 800 may generate a general model 820 relating conversational inputs to conversational outputs, which may be used to generate conversational outputs; this may be implemented according to any process for implementing machine-learning models 140 and/or language learning models as described in this disclosure. Alternatively or additionally, general learner 800 may include a lazy learning module 824. Lazy learning module 824 may be implemented according to any description in this disclosure for implementation of lazy learning modules.

With continued reference to FIG. 8, user communication learner 604 may include a user-specific learner 828, which may generate one or more modules that learn input-output pairs pertaining to communication with a particular user; a user specific learner may initially use input-output pairs established by general learner 800 and may modify such pairs to match optimal conversation with the particular user by iteratively minimizing an error function. User-specific learner 828 may include any elements suitable for use in any machine-learning module and/or learner as described in this description, including without limitation an unsupervised learning module 832 and/or a supervised learning module 836. User-specific learner 828 may generate a user-specific model 840 relating conversational inputs to conversational outputs, which may be used to generate conversational outputs; this may be implemented according to any process for implementing machine-learning models 140 and/or language learning models as described in this disclosure. Alternatively or additionally, user-specific learner 828 may include a lazy learning module 844. General learner 800 and/or user-specific learner 828 may initialize, prior to training, using one or more records retrieved from default response database 600 as described above.

Referring again to FIG. 6, processing module 508 may be further configured to determine that the at least a query includes an informational query and generate an informational response using the informational query. This may be performed, as a non-limiting example, by user communication learner 604, which use corpus to relate queries to labels identifying conversational queries or informational queries. Alternatively or additionally, parsing module 504 may provide processing module 508 information indicating that a query is a conversational query and/or an informational query. Generation of an informational response may be accomplished by retrieving at least a datum from an informational resource, which for purposes of this disclosure is a data structure, database, data store, and/or data module that returns data usable to generate an informational response when queried using an informational query. For instance, and without limitation, processing module 508 may be configured to retrieve at least a datum from a behavior modification model 124 using the informational query and generate the informational response using the at least a datum. As a non-limiting example, processing module 508 and/or a behavior modification database 128 may compare informational query to one or more textual elements in behavior modification model 124; comparison may be performed using any form of textual comparison and/or matching described above as performed by parsing module 504, processing module 508, and/or language processing module 144.

Still referring to FIG. 6, as a non-limiting example, informational query may include one or more words or phrases describing actions, persons, places, things and/or substances mentioned in a textual message sent to or from user client device 112. For instance, if an incoming message states "Hey, want to go to the park and get ripped?" an information query may include the phrases and words "go to the park," "get ripped," "want," "want to go,"; these may be used to retrieve behavior modification data from one or more resources as described in further detail below. As another non-limiting example, metadata may be turned into an informational query; for instance, metadata may indicate that a user client device 112 is receiving a text from, and/or sending a text to, a particular person; an informational query may be generated to determine whether that person is identified as associated with a problematic behavior and/or a goal behavior. As a further non-limiting example, metadata may include a location to which a user client device 112 is traveling according to, for instance, navigation instructions and/or at which a user client device 112 is located based on GPS or the like; an informational query may be generated to determine whether that location is associated with problematic behaviors or goal behaviors. Persons skilled in the art, upon reviewing the entirety of this disclosure, will be aware of various additional examples of data that may be incorporated in informational queries as contemplated in this disclosure.

Still referring to FIG. 6, generating the informational response using at least a datum from a diagnostic output may include generating the informational response and/or a portion thereof directly from the at least a datum; for instance, processing module 508 may convert the at least a datum into narrative language, images, and/or videos using any element of plan generation module as described above, and may incorporate the narrative language, images, and/or videos into the informational response. Alternatively or additionally, generating the informational response using at least a datum from a diagnostic output may include modifying the informational query using the at least a datum and performing any step described herein for generating an informational response from an informational query using the modified informational query.

With continued reference to FIG. 6, processing module 508 may be configured to retrieve at least a datum from a user database 148 using the informational query and generate the informational response using the at least a datum. For instance, and without limitation, processing module 508 may query locations table 400 to determine whether user has any behavior modification data relating to a location listed in metadata and/or described in textual data. As a further non-limiting example, processing module 508 may query person table 404 to determine whether a person listed in textual data and/or described in metadata is associated with any element of behavior modification data for a user of user client device 112. As an additional non-limiting example, processing module 508 may query history table 412 to determine whether any term in textual data and/or metadata is associated with any user history. As a further non-limiting example, processing module 508 may submit any or all words and/or phrases from textual data or metadata to terminology table 408 to determine user-specific meanings and/or association with data in other tables.

Still referring to FIG. 6, generating the informational response using at least a datum from a user database 148 may include generating the informational response and/or a portion thereof directly from the at least a datum; for instance, processing module 508 may convert the at least a datum into narrative language, images, and/or videos using any element of plan generation module as described in further detail below, and may incorporate the narrative language, images, and/or videos into the informational response. Alternatively or additionally, generating the informational response using at least a datum from a user database 148 may include modifying the informational query using the at least a datum and performing any step described herein for generating an informational response from an informational query using the modified informational query.

Continuing to refer to FIG. 6, processing module 508 may be further configured to retrieve at least a datum from a behavior modification database 128 using the informational query and generate the informational response using the retrieved at least a datum. For instance, and without limitation, processing module 508 may query user data table 200 to find information linking user to one or more words or phrases in informational query, and/or to find associations with data retrieved from user database 148 as described above. As an additional non-limiting example, processing module 508 may query locations table 204 to determine whether user a location described in textual data and/or metadata is associated with one or more behavioral modification data as described above. As a further non-limiting example, processing module 508 may query problematic entity table 208 to determine if there is a problematic entity matching one or more data from informational query. Similarly, processing module 508 may query positive entity table 212 to determine if there is a positive or helpful entity matching one or more data from informational query.

Still referring to FIG. 6, generating the informational response using at least a datum from behavioral database may include generating the informational response and/or a portion thereof directly from the at least a datum; for instance, processing module 508 may convert the at least a datum into narrative language, images, and/or videos using any element of plan generation module as described in further detail below, and may incorporate the narrative language, images, and/or videos into the informational response. Alternatively or additionally, generating the informational response using at least a datum from a behavioral database may include modifying the informational query using the at least a datum and performing any step described herein for generating an informational response from an informational query using the modified informational query.

Alternatively or additionally, processing module 508 may be configured to input the informational query to a behavior modification learner 136 operating on the at least a server, wherein the behavior modification learner 136 is designed and configured to generate behavior modification data as a function of a training set correlating user input data to behavior modification data and the informational query, receive, from the behavior modification learner 136, the behavior modification data, and generate the informational response using the behavior modification data. Any pattern of data, including any words, phrases, collections of words and/or phrases in conversations, metadata, and/or combination of metadata with textual data may be converted into an input to behavior modification learner 136 and/or machine-learning model 140; machine-learning models 140 and/or processes as described above may then be used to generate an output listing one or more elements of behavior modification data.

With continued reference to FIG. 6, processing module 508 may be configured to generate the at least an informational response by generating a plurality of informational responses using a first informational resource, retrieving at least an additional datum from at least a second informational resource, and selecting an informational response using the at least an additional datum. This may include, without limitation, elimination from the plurality of informational responses of one or more informational responses that are inconsistent with the at least an additional datum. As a non-limiting example, second resource may include, for instance, user database 148, which may eliminate from any such list one or more elements that contradict one or more user data. For instance, a given geographical location may include both a church and an illicit massage parlor in a strip mall; user database 148 may indicate that the user is visiting the former and not the latter, eliminating a likely problematic behavior associated with the massage parlor. Persons skilled in the art, upon reviewing the entirety of this disclosure, will be aware of the enormous variety of other factors that may be used to eliminate one or more informational responses of a plurality of informational responses. Alternatively or additionally, selection of an informational response may be performed positively, for instance by matching the informational response to the at least a second datum. For instance, and without limitation, user database 148 may list data such as locations, entities, user history, or the like matching one or more elements of informational query, and indicating a higher likelihood that one behavior of a plurality of potential behaviors is indicated than another. Matching, whether performed negatively or positively, may be performed via any process described in this disclosure for matching one textual element to another, including string comparison, exact matching, detection of vector similarity, such as without limitation cosine similarity, above a threshold amount, or the like.

Still referring to FIG. 6, second information resource may include user client device 112; in an embodiment, processing module 508 may generate a user clarification question, provide the user clarification question to the user client device 112, and receive a user response from a user client device 112 via the user client module. Generating the clarification question may be performed using any suitable process for generating a conversational response as described above and/or any process for generating a combined conversational and informational response as set forth in further detail below. For instance, and as a non-limiting illustration, default response database 600 may contain a response template instructing artificial intelligence advisor 152, given variables stored in "option_1" and "option_2," to concatenate string and variable values in the following form: "Did you mean"+option_1+"or"+option_2+"?" so as to receive a user clarification. Similar templates could be constructed asking a user if her or she prefers an option stored in a first variable to an option stored in a second variable, or the like. Generation of clarification question may include identifying a difference between a first informational response and a second informational response and forming a question for a user asking about the difference. For instance, where a user enters textual information making up a direct question to artificial intelligence advisor 152, and results of informational and/or conversational query indicate two or more possible meanings of and/or informational matter connected to the question and/or words contained therein, either and/or both possible meanings may be provided to user client device 112. Similarly, where a user of user client device 112 is engaged in a communication with another person in textual form, or in the form of a voice conversation converted to text, artificial intelligence advisor 152 may generate informational queries based on such text, and informational resources as described above may indicate two or more possible meanings associated with text. As an illustrative example, a text containing an invitation to "get ripped" may generate a first possible meaning as an invitation to exercise for the purpose of accentuating muscle mass or definition, and a second meaning indicative of an offer to consume mood-altering substances to the point of extreme intoxication; artificial intelligence advisor 152 may attempt to determine which meaning is more likely based on additional queries of informational resources such as user database 148, or may alternatively or additionally generate a message asking the user which meaning is correct in this context. This approach for generating a request may be accomplished, without limitation, by dividing text describing each informational response, such as text obtained from a default response database, into tokens such as words or phrases, and using a similarity test such as vector similarity to detect one or more dissimilar tokens between two or more informational responses; the one or more dissimilar tokes may then be used to generate a conversational response as described above. Alternatively or additionally, more user input data may be collected and used in an iterative or aggregate fashion to determine a meaning matching the larger collection of user input data using more database queries and/or pattern matching via machine learning as described above.

Continuing to refer to FIG. 6, processing module 508 may be configured to convert an informational response into at least a portion of a textual output; this may be performed using any process and/or processes as described above for converting diagnostic outputs to narrative language, images, videos, and/or combinations thereof in plan generator or the like. For instance, and without limitation, processing module 508 may retrieve one or more strings and/or templates to generate a narrative language form of or analog to an informational output. Processing module 508 may generate result by reference to default response database 600 to acquire one or more textual, visual, or other responses. As noted above, general and/or user-specific learner may continue to populate default response database 600 and to use entries retrieved therefrom to assemble new responses in combination with machine learning methods. As a non-limiting example, a default response recovered from default response database 600 may include, without limitation, a statement such as "are you sure you want to do this?" As another example, a default response may include a template such as "are you sure you want to <insert language>" where "<insert language>" might include "visit her again," "go back to that bar," "eat that," or other phrases as determined by user history, behavioral modification requests or the like. Another example of a potential response may be a restatement of a behavioral goal, such as: "Your goal was to stop seeing prostitutes," or "Your goal was go to church at this time" or the like. Another response, which might be stored in default response table, may be one or more elements of inspirational text or image, such as an image of a user's children, a biblical quote, a recording of the user pledging to avoid and/or practice a particular behavior, or the like. Alternatively or additionally, generating the informational response using behavioral modification data may include modifying the informational query using the behavioral modification data and performing any step described herein for generating an informational response from an informational query using the modified informational query.

Still referring to FIG. 6, in an embodiment, processing module 508 may be configured to determine that the at least a query includes a conversation language query and an informational query, generate a conversational response using the conversational language query; generate an informational response using the informational query, and combine the conversational response and the informational response. Determination may be performed as described above. In an embodiment, processing module 508 may generate each of conversational response and informational response as described above. Conversational response and informational response may be combined in any suitable manner. For instance, where conversational response and informational response are two separate sentences, clauses, or sequentially arrangeable phrases, combination may include concatenation; as a non-limiting illustration, conversational response may include an initial sentence such as "Hi. Just checking in." and a final sentence such as "Are you sure you want to do that?" and informational response may include a statement such as "You seem to be going back to the massage parlor." which processing module 508 may combine into "Hi. Just checking in. You seem to be going back to the massage parlor. Are you sure you want to do that?" As a further non-limiting example, conversational response may include a template, as described above, into which an informational response may be inserted. As a non-limiting illustration, conversational response may be "It looks like you are about to <INFO>." and informational response, which processing module 508 may use to replace "<INFO>" may be a phrase describing an action such as "smoke methamphetamine again"; replacement may be performed as described above. Templates may be nested and/or concatenated; for instance a variable or label calling for insertion of a textual value into a template may itself refer to an additional template to be inserted at that point. Persons skilled in the art, upon reviewing the entirety of this disclosure, will be aware of various ways in which conversational responses and informational responses may be combined to produce textual output. The use of particular formats to indicate fields to be occupied by informational responses as above is provided for the sake of illustration only; templates may have any suitable structure and/or demarcation that may occur to persons skilled in the art upon reviewing the entirety of this disclosure.

Artificial intelligence advisor 152 may be configured to transmit at least a textual output to a user client device 112; at least a textual output may include any textual data, including without limitation an answer to a user, which may be generated as described above. At least a textual output may be output to a user in any suitable way, including display on a screen, text-to-speech audio output, or the like. Receipt of at least a user input and/or transmission of at least a textual output maybe performed repeatedly and/or iteratively; for instance, receipt of user inputs and provision of textual outputs may be performed multiple times during a conversation between user and advisory module.

Referring again to FIG. 5, artificial intelligence advisor 152 may include a consultation initiator 512 configured to detect a consultation event in a user textual conversation and initiate a consultation with an informed advisor as a function of the consultation event. A consultation event, as used herein, is a situation where a person besides a user is needed to address the user's situation or concerns, such as when a user needs moral or emotional support from a friend or family member, intervention by a friend, family member, or professional, and/or professional services to aid in preventing problematic behavior and/or encouraging goal behaviors. Detection may be performed, without limitation, by matching an input and/or set of inputs to an output that constitutes an action of initiating a consultation; such a pairing of an input and/or input set may be learned using a machine learning process, for instance via general learner and/or user specific learner. In the latter case, information concerning a particular user's behavior modification request, problematic behaviors, and/or goal behaviors may be a part of the training set used to generate the input/input set to consultation event pairing; for instance, failure of a user to attend a church function, addition support meeting, or the like may be associated with an output requiring a consultation event. As a further example, textual data and/or metadata indicating that user is in the process of relapsing or otherwise engaging in a problematic behavior may match to an output indicating a consultation event. Initiation of consultation may include transmitting a message to an advisor device associated with an appropriate expert, or person acting in such a role, such as without limitation transmission of information regarding a needed consultation to family members, doctors, consultants, church members, members of addition support groups, or the like; such a message may indicate a current or intended location of user, and invite one or more such persons to come to where the user, contact the user via the user client device 112, or otherwise intervene in the behavior of the user. Initiation of consultation may alternatively or additionally include providing an output to the user informing the user that a consultation with an expert, who may be specified by name or role, is advisable. Consultation initiator 512 may analyze consultation inputs, defined as any element of conversation input to, output from, and/or processed by artificial intelligence advisor 152 and/or any component or module thereof, including without limitation user inputs, words or phrases extracted from user inputs conversational queries, informational queries, conversational outputs, informational outputs, and/or textual outputs. In an embodiment, consultation initiator may compare consultation inputs to keywords in a keyword listing 516, where keywords may include any word or phrase as described in this disclosure, and comparison may include any form of comparison as described in this disclosure. Keyword listing 516 may include any data structure and/or database suitable for storage, retrieval, and/or comparison of textual data. Keyword listing 516 may be populated using expert submissions of keywords associated with consultation events; expert submissions may be collected and inserted to keyword listing 516 using any methods, components, and/or modules as described above regarding expert knowledge database 304 and/or related elements. Keyword listing 516 may include user-specific keywords; for instance, keyword listing may combine keywords with behavior modification data and/or user identifiers, such that a keyword encountered for a particular user, and/or for a user having a particular condition and/or prognosis, may generate a consultation event, while absent such matching data the keyword may not generate a consultation event.

Figure 9:
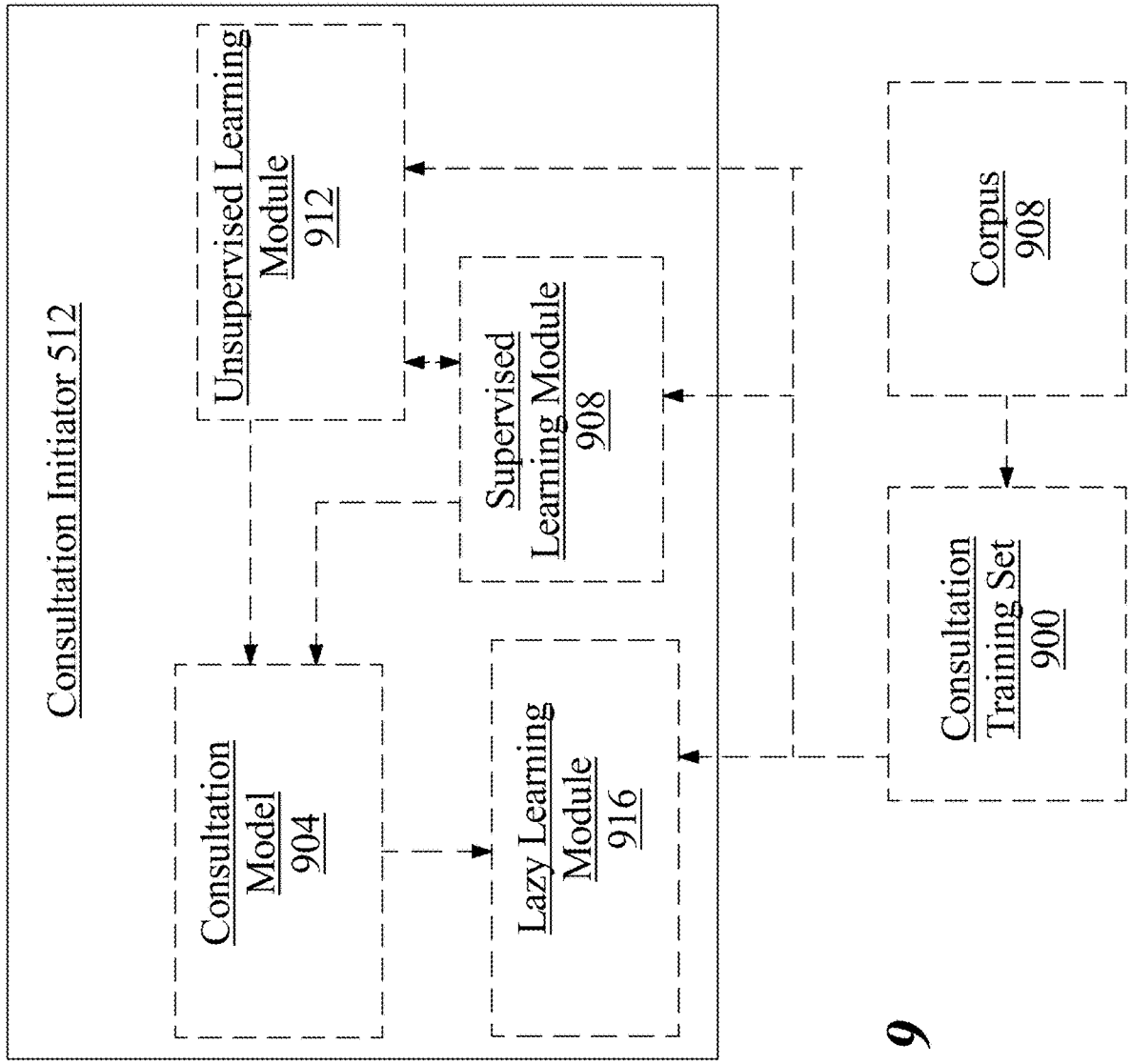
FIG. 9 is a block diagram illustrating an exemplary embodiment of a consultation initiator.

Referring now to FIG. 9, consultation initiator 512 may alternatively or additionally perform one or more machine-learning operations to detect consultation events. In an embodiment, consultation initiator may perform machine-learning operations using a consultation training set 900, which may be any training set as described in this disclosure. Consultation training set may, as a non-limiting example, include a plurality of entries, each entry including an input having a word or phrase and an output indicating a category of consultation event; category of consultation event may include no consultation event, a need for textual communication, a need for in-person intervention or contact, and/or a need to call police, emergency personnel, or the like. Consultation training set 900 may be assembled using, without limitation elements from corpus 808 of conversations as described above, combined with data describing outcomes for users engaged in such conversations; outcomes may be entered by informed advisors who dealt with outcomes. Additional users of system 100 may alternatively or additionally enter outcome information from records or the like.

Still referring to FIG. 9, consultation initiator 512 may generate outputs indicating a consultation event, or absence of a consultation event, using at least a user entry and consultation training set. This may be performed according to any machine-learning process as described in this disclosure, such as without limitation any machine-learning process performed by prognostic label learner and/or language processing module 144. Consultation initiator 512 may generate a consultation model 904 relating conversation text to consultation events. For instance, and without limitation, consultation initiator 512 may be configured to perform one or more supervised learning processes, as described above; supervised learning processes may be performed by a supervised learning module 908, which may be any supervised learning module as described in this disclosure. Inputs to supervised learning module 908 may include, without limitation words or phrases from corpus 808, while outputs may include categories of consultation events. Consultation initiator 512 may perform one or more unsupervised machine-learning processes as described above; unsupervised processes may be performed by an unsupervised learning module 912, which may be any unsupervised learning nodule as described in this disclosure. Unsupervised learning module 912 may, for instance, detect correlations between keywords from keyword listing 516 and/or words or phrases from corpus 808 that supervised learning module 908 has associated with consultation events, and other words and phrases, to add additional keywords and/or potential words/phrases that may trigger consultation.

Continuing to view FIG. 9, consultation initiator 512 may be configured to perform a lazy learning process as a function of the consultation training set 900 at least a user input. Lazy learning processes may be performed by a lazy learning module 916 executing on at least a server and/or on another computing device in communication with at least a server, which may include any hardware or software module.

In an embodiment, and still viewing FIG. 9, machine-learning processes and/or modules of consultation initiator 512 may be combined with keyword detection. For instance, machine-learning processes and/or outputs may be triggered upon keyword detection or may operate in parallel or independently from keyword-detection processes. Machine-learning may supplement keyword detection; for instance, and without limitation there may be some keywords that definitely cause consultation events, or there may be keywords that are not enough by themselves to trigger consultation, but may trigger consultation if combined with another detection, which may include a machine-learning output and/or detection of an additional keyword. Machine-learning processes may add keywords when a certain keyword is repeatedly found to be linked to a consultation event, such as without limitation if a linear regression analysis or the like maps a single word or phrase, and/or a combination of one phrase with one prognostic label or one category of prognostic label and/or user datum; such detected keywords may be added to keyword listing 516 by consultation initiator 512. Consultation initiator 512 may automatically place an emergency call for one or more consultation events; for instance and without limitation, keyword listing 516 and/or consultation model 904 may include flags indicating that a detected consultation event requires an emergency call. User database 148 or any other suitable database may list one or more numbers to place emergency calls to, for instance using voice-over-internet-protocol (VoIP) or other automatic telephonic call protocols.

In an embodiment, and referring again to FIG. 5, where artificial intelligence advisor 152 and/or consultation initiator 512 detects a consultation event, artificial intelligence advisor 152 and/or consultation initiator 512 may select at least an expert from an expert list 520 and transmit a message to the at least an expert based on the detected consultation event. At least an expert may be any person identified by system 100 as able to assist a user with behavior modification as described above. At least an expert may include any individual that may aid a user in achieving user's behavior modification by providing assistance to a user such as by providing encouragement, support, mentorship, guidance, and/or services. An expert may include for example an informed advisor, family, friends, members of the community, members of a support group, coaches, religious leaders, health advisors such as nutritionists or addiction therapists, co-workers, acquittances and the like. An expert may include for example, a nutritionist, a health coach, an addiction specialist, a close family friend, a church member, a participant at a 12-step program such as alcoholics anonymous or narcotics anonymous, and the like. Expert list 520 may include any suitable database, data store, or other data structure as described in this disclosure. Expert list 520 may include at least an expert selected to aid a given user with that user's behavioral modification needs; expert list 520 may return one or more experts based on informational queries and/or queries identifying behavioral modification data as described above.

Still referring to FIG. 5, system 100, at least a server 104, and/or artificial intelligence advisor 152 may add at least an expert to expert list 520 based on one or more expert qualities. An "expert quality" as used herein includes any attribute or characteristic exhibited by at least an expert. Expert qualities may include for example positive qualities that a user may desire in an expert such as trustworthiness, vigilance and/or watchfulness, wisdom, loyalty, unconditional love, supportiveness, reliability, self-control, rejecting evil, kindness, truthfulness, ability to give good advice, positive influence, cooperative, attitude of service, knowledge about user, family commitment, high standards, share burdens, encouraging user to trust in a higher power, humility, forgiveness, peacefulness, acceptance, and/or generosity. Expert qualities may include for example negative qualities that a user seeks to avoid in an expert such as drunkenness, filthy language, corruption, malice, deceit, hatred, jealousy, greed, and the like. For example, a user who is experiencing opioid addictions may generate at least a request for an expert who portrays qualities such as unconditional love, positive influence, and encouraging user to trust in a higher power while avoiding at least an expert who exhibits qualities such as negativity, deceit, and drunkenness. In yet another non-limiting example, a user who is obese and desires to lose weight may generate at least a request for an expert who portrays qualities such as supportiveness and reliability and who does not portray qualities such as greed or lack of self-control.

With continued reference to FIG. 5, artificial intelligence advisor 152 may include an expert module 524 operating on the at least a server. Expert module 524 may include any suitable hardware or software module. Expert module 524 may be designed and configured to generate at least an expert list 520 as a function of the at least an expert quality and the at least a request for a behavior modification, receive at least a user input as a function of the at least an expert list 520, generate at least a request for the selected expert, and transmit the at least a request for the selected expert. Generating at least an expert list 520 may include matching at least an expert to at least an expert quality.

With continued reference to FIG. 5, expert module 524 may include expert learner 528; the expert learner 528 may be designed and configured to generate at least an expert list 520 as a function of the at least an expert quality and the at least a request for a behavior modification. Expert learner 528 may include any hardware and/or software module. Expert learner 528 may be designed and configured to generate outputs using machine learning processes as described above.

Still referring to FIG. 5, expert learner 528 may be designed and configured to generate at least an expert list 520 by creating at least a first machine-learning model 140 relating expert qualities to behavior modifications using a training set and generating at least an expert list 520 using the first machine-learning model 140; at least a first machine-learning model 140 may include one or more models that determine a mathematical relationship between expert qualities and behavior modifications. Training set includes any of the training sets as described below in more detail in reference to FIG. 5. An expert list 520 as used in this disclosure is a data structure containing a suggestion as to experts that may be able to aid a user in overcoming and/or having a particular behavior modification stabilize or go into remission. Expert list 520 may include suggested experts that may provide support, encouragement, advice, and/or services for a user. For example, expert list 520 may include a functional medicine doctor, a health coach, and an addiction specialist for a user with a pornography addiction. In yet another non-limiting example, expert list 520 may include a pastor, a church member, and a religious teach for a user with a desire to learn more about the Christian faith. Machine-learning models 140 may include without limitation any machine-learning algorithms as described above and/or any combination of such algorithms.

With continued reference to FIG. 5, machine-learning algorithms may generate expert list 520 as a function of a classification of at least a behavior modification. Classification as used herein includes pairing or grouping behavior modifications as a function of a shared commonality. Classification may include for example, groupings, pairings, and/or trends between behavior modifications and proposed experts, future need for a particular expert, and the like. In an embodiment, machine-learning algorithms may examine relationships between a future propensity of a user to require a new expert based on current requests for behavior modifications. Machine-learning algorithms may include any and all algorithms as performed by any modules, described herein for expert learner 528. For example, machine-learning algorithms may relate a behavior modification such as a gambling addiction to a user's future propensity to require a particular expert such as a pastor or religious figure who may be able to provide moral guidance for a user with a gambling addiction. Machine-learning algorithms may examine precursor behavior modifications and future propensity to report a subsequent behavior modification. For example, machine-learning algorithms may examine a user with a behavior modification such as alcoholic addiction with a future propensity to report a subsequent behavior modification such as opioid addiction. In yet another non-limiting example, machine learning algorithms may examine varying degrees of behavior modifications. For example, machine-learning algorithms may examine a behavior modification for a food addiction with a future propensity to report a less restrictive food addiction such as a cake addiction or a soda addiction. In yet another non-limiting example, machine-learning algorithms may examine a behavior modification with a future propensity to report a more restrictive behavior modification such as a request for a behavior modification to develop a fitness regimen with a subsequent request for a request for a behavior modification to attend six fitness classes each week. Machine-learning algorithms may examine behavior modification requests by categories, such as physical addictions, personal health goals, spiritual goals, emotional addictions, psychiatric behaviors, fitness goals, and the like. For example, machine learning algorithms may examine user behavior modifications for diagnosed psychiatric conditions such as obsessive-compulsive disorder (OCD), explosive personality disorder, and bipolar disorder versus behavior modifications for physical addictions such as alcohol, barbiturates, food, nicotine, pornography, and gambling. Machine-learning algorithms may examine behavior modifications among categories of users such as behavior modifications in men between the ages of 45-55 in Alaska versus user behavior modifications among females age 18-24 in Alabama. Machine-learning algorithms may examine trends among behavior modifications such as for example, a behavior modification for a benzodiazepine addiction and a subsequent alcohol addiction.

Continuing to refer to FIG. 5, expert learner 528 may generate a plurality of expert list 520s having different implications for a particular person. For instance, where the at least a request for a behavior modification includes a request for an addiction such as alcohol, drugs, sex, pornography, gambling, and the like, expert list 520 may be consistent with recommendations for consultation with experts including functional medicine doctors, 12-step program directors, and other addicts. In such a situation, expert learner 528 and/or server 104 may perform additional processes to resolve ambiguity. Processes may include presenting multiple possible results to a user, informing the user that one or more user preferences are needed to determine a more definite expert list 520, such as a user preference for a functional medicine approach to treatment or a peer centered approach to treatment such as a 12-step program or both. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, expert learner 528 and/or server 104 may operate a further algorithm to determine which of the multiple outputs is most likely to be correct; algorithm may include use of an additional supervised and/or unsupervised model. Alternatively or additionally, expert learner 528 may perform one or more lazy learning processes using a more comprehensive set of user data to identify a more probably correct result of the multiple results. Results may be presented and/or retained with rankings, for instance to advise a user of the relative probabilities of various expert list 520 being correct; alternatively or additionally, expert list 520 associated with a probability of correctness below a given threshold and/or expert list 520 contradicting results of the additional process, may be eliminated. As a non-limiting example, a behavior modification for a personal spiritual goal such as developing a religious practice may lead to experts such as functional medicine doctors and 12-step program directors from being eliminated from an expert list 520 for a user while experts such as pastors, religious teachers, and church goers may be retained. Persons skilled in the art, upon reviewing the entirety of this disclosure, will be aware of various ways in which additional processing may be used to determine relative likelihoods of experts on a list of experts, and/or to eliminate some experts from such a list. Expert list 520 may be provided to a user such as at user client device 112 and/or advisor client device 116.

With continued reference to FIG. 5, expert module 524 may include expert database 532. Expert database 532 may include any database or datastore suitable for use as language database as described above. Expert database 532 may include one or more categories of experts as described in more detail below. Expert database 532 may include a table containing information such as one or more qualities of a particular expert or category of expert. Expert learner 528 may consult expert database 532 to generate expert list 520. For example, expert learner 528 may consult expert database 532 to match a particular expert and/or category of expert to an expert quality. Matching may include selecting an expert that exhibits a particular quality. For example, an expert such as a 12-step member attendee may be matched to a quality such as self-control and positive influence. Matching may include selecting an expert that does not exhibit an undesirable quality. For example, an expert such as a functional medicine doctor may be matched as an expert if the functional medicine doctor does not exhibit qualities such as sexual immorality or debauchery.

Qualities as to an expert may be collected and stored in expert quality database which may be located within expert module 524. Qualities of at least an expert may be self-reported, such as a when at least an expert may enter information about himself or herself into system 100 such as at first GUI and/or second GUI. For example, at least an expert who has been faithful to one's spouse may self-report a quality such as faithfulness and joy. At least an expert who has had affairs and sexual impurity may self-report a quality such as sexual immorality. In an embodiment, at least an expert may self-report a quality on a scale of how often they may exhibit a certain quality. For example, a scale may include categories describing how often an expert exhibits a quality such as a category of "never" when an expert never exhibits a quality, a category such as "rarely" when an expert may infrequently exhibit a quality, a category such as "sometimes" when an expert may exhibit a quality more frequency, a category such as "frequently" when an expert is repeatedly exhibiting a quality, and a category such as "always" when an expert is consistently exhibiting a quality.

In an embodiment, qualities may be reported about an expert by an expert's network which may include an expert's family, friends, acquaintances, and other users an expert has provided support to. For example, a user that an expert helped achieve a behavior modification such as recovering from alcohol addiction may rate and provide an input as to qualities that expert may possess and/or exhibit. In such an instance, user may report to system 100 that expert exhibited qualities such as patience, kindness, and self-control. Qualities as reported by an expert's network may also be ranked on a scale as described above as to how often an expert exhibits a quality. Qualities of at least an expert may also be obtained and stored in a database from an expert's self-reflection of qualities expert may exhibit. Qualities stored in a database as to an expert may be aggregated together when results are received from different evaluators. Qualities stored in a database may be frequently updated to reflect different qualities an expert may exhibit, and/or different frequencies that an expert may exhibit a quality. For example, an expert who sometimes exhibits joy, may frequently experience joy after a personal achievement such as graduation from culinary school and landing a dream job and as such database may be updated to reflect this. In yet another non-limiting example, an expert who frequently exhibits drunkenness and then enters rehab and recovers may have database updated to reflect that expert never experiences drunkenness anymore.

With continued reference to FIG. 5, selecting at least an expert may include producing a field of combinations of experts and selecting at least an expert using a lazy-learning process. Lazy-learning process may include any of the lazy-learning process as described above. Lazy-learning process may include for example, k-nearest neighbors algorithm, a lazy naive Bayes algorithm, or the like; persons skilled in the art, upon reviewing the entirety of this disclosure, will be aware of various lazy-learning algorithms that may be applied. Lazy-learning process may include a continuously updating mathematical expression such as continuously updating training sets with new entries based on one or more user entries. User entries may update mathematical expressions, and subsequently be utilized to generate a new training set to modify the new expression. In an embodiment, lazy-learning process may include performing a k-nearest neighbors algorithm, so as to predict the classification of a new sample point based on already known data or training data. In an embodiment, k-nearest neighbors algorithm may assign a weighted contribution of each neighbor, so that nearer neighbors contribute more to the average than the more distant ones. For example, a weighting scheme may include giving each neighbor a weight of 1/d where d is the distance to the neighbor. The neighbor may include a set of data for which the class is known, such as training data. In an embodiment, k-nearest neighbors algorithm may include using training data such as vectors in a multidimensional space, each containing a class label. The training data initially used to generate the k-nearest neighbors algorithm may include a training data that includes the vector and correlated class label. In an embodiment, subsequent data may be classified during the classification phase, whereby k is a user-defined constant based on the training data and a subsequent unlabeled vector is classified by assigning a class label that is most frequent among the k training samples nearest to that vector space. In an embodiment, vector space may be measured using Euclidean distance. In an embodiment, classification accuracy calculations based on k values may be updated using algorithms including Large Margin Nearest Neighbor and/or Neighborhood components analysis. In an embodiment, neighbors may be selected using brute force calculated based on Euclidean distance from point of interest whose class label is unknown to points contained within training set. Distance may also be measured utilizing other norms including for example cosine similarity between vectors. In an embodiment, neighbors may be selected utilizing tree like data structures to determine distances from points of interest to points contained within training sets. In an embodiment, distances may be computed by plotting in "n-dimensional" space as defined by any suitable coordinate system including without limitation Cartesian and polar, an n-dimensional vector space, or the like, where points represent data values.

With continued reference to FIG. 5, k-nearest neighbors algorithms may select k values with varying values. Larger values of k may reduce the effect of noise on classification of neighbors while making explicit boundaries between classes less distinct. K values may be calculated utilizing heuristic techniques including hyperparameter optimization. K values may be calculated utilizing bootstrapping methods.

With continued reference to FIG. 5, classification utilizing k-nearest neighbor algorithms may be useful to select optimal experts based on weighted contributions of datasets containing experts and expert qualities. Distances between known datasets may be utilized to label subsequent datasets including experts and expert qualities utilizing any of the methodologies as described herein. Such calculations may aid in selecting optimal experts.

With continued reference to FIG. 5, selecting at least an expert may include generating a loss function of user specific qualities and minimizing the loss function. In an embodiment, expert module 524 may compare one or more expert options and one or more expert qualities to a mathematical expression representing an optimal combination of user entered variables. Mathematical expression may include a linear combination of variables, weighted by coefficients representing relative importance of each variable in selecting an optimal expert exhibiting an optimal quality and/or not exhibiting unfavorable qualities. For instance, a variable such as exhibiting a quality such as having patience may be multiplied by a first coefficient representing the importance of having patience, a second variable such as having a faith based practice may be multiplied by a second coefficient representing the importance of having a faith based practice, a degree of variance from a quality such as not self-seeking may be represented as another parameter, which may be multiplied by an additional coefficient representing an importance of that variable; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

With continued reference to FIG. 5, mathematical expression may represent a loss function, where a "loss function" is an expression of an output of which an optimization algorithm minimizes to generate an optimal result. As a non-limiting example, expert module 524 may calculate variables of each of a plurality of experts and/or expert qualities, calculate an output of mathematical expression using the variables, and select an expert that produces an output having the lowest size, according to a given definition of "size" of the set of outputs representing each of the plurality of experts; size may, for instance, include absolute value, numerical size, or the like. Selection of different loss functions may result in identification of different expert list 520 and generating minimal outputs; for instance, where having patience is associated in a first loss function with a large coefficient or weight, having faith is associated with a small coefficient or weight, may minimize the first loss function, whereas a second loss function wherein having patience has a smaller coefficient but degree of variance from having faith has a larger coefficient may produce a minimal output for a different expert list 520 and having more importance on having patience but more closely hewing to having faith.

Alternatively or additionally, and still referring to FIG. 5, each expert list 520 may be represented by a mathematical expression having the same form as mathematical expression; expert module 524 may compare different expert list 520 using an error function representing average difference between the two mathematical expressions. Error function may, as a non-limiting example, be calculated using the average difference between coefficients corresponding to each variable. Expert list 520 having a mathematical expression minimizing the error function may be selected, as representing an optimal expression of relative importance of variables to a system or user. In an embodiment, error function and loss function calculations may be combined; for instance, a variable resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to variables. Coefficients of mathematical expression and/or loss function may be scaled and/or normalized; this may permit comparison and/or error function calculation to be performed without skewing by varied absolute quantities of numbers.

Still referring to FIG. 5, mathematical expression and/or loss function may be provided by receiving one or more user commands. For instance, and without limitation, a graphical user interface 120 may be provided to user with a set of sliders or other user inputs permitting a user to indicate relative and/or absolute importance of each variable to the user. Sliders or other inputs may be initialized prior to user entry as equal or may be set to default values based on results of any machine-learning processes or combinations thereof as described in further detail below. In an embodiment, a user specific variable may include a faith-based quality such as for example, an expert who practices the Christian based faith.

With continued reference to FIG. 5, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 5, mathematical expression and/or loss function may be generated using machine learning using a multi-user training set. Training set may be created using data of a cohort of persons having similar demographic, religious, health, behavior modification requests, and/or lifestyle characteristics to user. This may alternatively or additionally be used to seed a mathematical expression and/or loss function for a user, which may be modified by further machine learning and/or regression using subsequent user selections of experts, expert list 520, and/or expert qualities.

With continued reference to FIG. 5, selecting at least an expert may occur as a function of a user entered category of at least an expert. Category may include a class of individuals having shared characteristics. Category may include shared characteristics as to function that at least an expert may perform. For example, a user may request a category of at least an expert such as a functional medicine doctor, a family member, a friend, a member of the community and the like. Category of at least an expert may be categorized into sub-categories. For example, a category such as a functional medicine doctors may include primary care functional medicine doctors, gastrointestinal functional medicine doctors, psychiatric functional medicine doctors, dermatology functional medicine doctors and the like. In yet another non-limiting example, a category such as friends may be categorized into sub-categories which may include friends from childhood, friends from college, friends from work, friends from health club, friends from an activity such as an organized sport, friends from a support group, friends from a neighborhood and the like.

With continued reference to FIG. 1, expert module 524 may receive at least a user input selected at least a selected expert as a function of the expert list 520. User input, as used herein may include any user data including for example a user preference for at least an expert or a user dislike for at least an expert. User input containing the at least a selected expert may be utilized by expert module 524 to generate at least a request for the at least a selected expert.

In an embodiment, and still referring to FIG. 5, expert learner 528 may generate a plurality of expert lists 520 having different implications for a particular person. For instance, where a behavior modification indicates that a person has a pornography addiction, various experts may be generated within expert list 520 associated with helping the user enter remission for the behavior modification, including experts such as addiction specialists, functional medicine doctors, fitness coaches, meditation teachers, friends, family, and the like. In such a situation, expert learner 528 may include any and all such experts on expert list 520. In an embodiment, expert learner 528 may presenting multiple possible results to user and allowing a user to select an expert that user feels may be beneficial and help the user achieve user's behavior modification. In an embodiment, expert learner 528 may rank possible experts in some sort of order within expert list 520 such as including rank of what impact each expert may have on any particular behavior modification. For example, a user with a behavior modification such as shopping addiction may have an addiction specialist ranked high on expert list 520 while a user with a behavior modification such as a desire to lose seven pounds of body weight in anticipation of a wedding, may have an addiction specialist ranked very low if included at all but may have a fitness coach or weight loss professional ranked very high. Alternatively or additionally, processes may include additional machine learning steps. For instance, expert learner 528 may perform one or more lazy learning processes using a more comprehensive set of user data to identify a more probably correct result of the multiple results. Results may be presented and/or retained with rankings, for instance to advise a user of the relative probabilities of various experts being correct or ideal choices for a given person; alternatively or additionally, experts associated with a probability of success or suitability below a given threshold and/or experts contradicting results of the additional process, may be eliminated.

Figure 10:
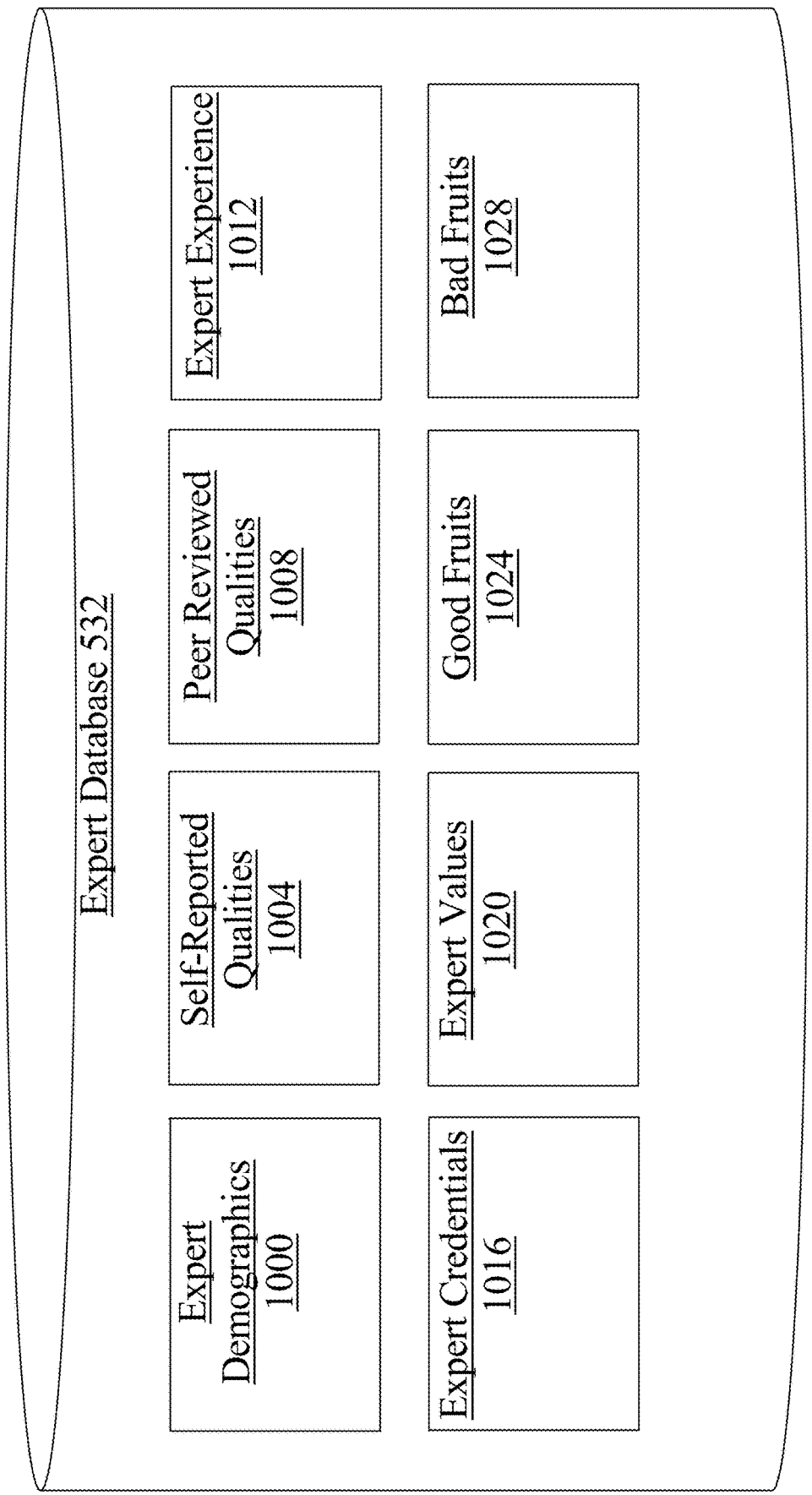
FIG. 10 is a block diagram illustrating an exemplary embodiment of an expert database.

Referring now to FIG. 10, an exemplary embodiment of expert database 532 is illustrated. Expert database 532 may include any database or datastore suitable for language database as described above. Expert database 532 may include one or more entries linking labels and/or information associated with one or more experts. Linking may be performed by reference to historical data concerning experts such as previous encounters and/or interactions with specific experts. Experts may include any of the experts as described herein. Experts may work together to create an inner support circle to provide encouragement, support, mentorship, guidance, and/or services to a user in response to a user's desired behavior modification. Experts may be selected based on qualities an expert may exhibit, as well as desired qualities a user is seeking in an expert as well as a user's preference for an expert such as an expert that is located within a certain geographical location that is accessible to user. In an embodiment, at least a request for a behavior modification may be linked to a maximum number of experts that may create a user's inner circle. For example, at least a request for a behavior modification such as a pornography addiction may be linked to a maximum number of ten to twelve experts, reflecting Jesus's twelve expert disciples in the Bible.

With continued reference to FIG. 10, one or more experts may be categorized based on one or more functions and/or qualities that an expert may exhibit. Family experts may include any family member of user who may provide encouragement, support, mentorship, guidance, and/or services to a user in response to user's desired behavior modification. Family experts may include experts who are descendants of a common ancestor as user. This may include for example immediate family members such as parents, siblings such as brothers and sisters, as well as immediate family such as aunts, uncles, cousins, grandparents, and the like. Family experts may include adopted family members such as when a child is adopted after being given up by birth parents or when a user has close friends who user considers to be part of user's family. For example, an adult aged user who may be orphaned after the death of both parents may consider a close friend's family to be user's adopted family if user attends holidays such as Thanksgiving or Christmas with close friend's family. Experts may include spiritual experts. Spiritual experts may include experts specializing in the conscious mind body connection who may provide encouragement, support, mentorship, guidance, and/or services to a user in response to user's desired behavior modification. Spiritual experts may include for example, religious leaders such as a pastor at a church, a rabbi at a synagogue, a member of the Buddhist community, an Inman and the like.

With continued reference to FIG. 10, experts include nutrition experts. Nutrition experts may include experts specializing in diet, nutrition, and/or supplementation who may provide encouragement, support, mentorship, guidance, and/or services to a user in response to user's desired behavior modification. Nutrition experts may include nutritionists, dieticians, chefs, certified nutrition specialist, nutrition coaches, and/or holistic health coaches. Nutrition experts may include for example, a registered dietician who may aid a user with a behavior modification such as weight loss to create customized meal plans to aid user in losing two pounds each week. Experts may include fitness experts. Fitness experts may include experts specializing in physical activities such as sports, exercise, movement, and/or activities of daily life who may provide encouragement, support, mentorship, guidance, and/or services to a user in response to user's desired behavior modification. Fitness experts may include for example, personal trainers, sports coaches, yoga instructors, group exercise instructors, athletic trainers, physical therapists, fitness instructors, authors of fitness instruction books or manuals, experts in kinesiology, and/or experts skilled in anatomy and/or biomechanics. For example, a fitness expert such as a physical therapist may provide guidance to a user with a desired behavior modification to recover from an injury such as planter fasciitis and/or a bone bruise.

With continued reference to FIG. 10, experts may include functional medicine experts. Functional medicine experts may include experts specializing in the practice of functional medicine who may provide encouragement, support, mentorship, guidance, and/or services to a user in response to user's desired behavior modification. Functional medicine experts may include for example, medical doctors, osteopathic medicine doctors, nurse practitioners, physician assistants, chiropractic doctors, naturopathic doctors, pharmacists, nurses, licensed practical nurses, psychologists, respiratory therapists, social workers, x-ray technicians, pharmacy technicians, mental health professionals, medical assistants, and the like. For example, a functional medicine expert such as a physician assistant may provide mentorship to a user with a behavioral modification that includes heroin addiction as the user initially detoxes off heroin. Experts may include friend experts. Friend experts may include friends of user who may provide encouragement, support, mentorship, guidance, and/or services to a user in response to user's desired behavior modification. Friends may include a person whom a user knows and with whom a user has a bond of mutual affection. Friends may include persons from different aspects of a user's life such as friends from user's work, friends from user's childhood, friends from user's college, friends from user's graduate school, friends from user's neighborhoods, friends from user's spiritual community, friends from user's organized sports, friends from user's knitting circle and the like. For example, a friend of user from childhood may provide support and encouragement for a user with a behavior modification such as a desire to recover from anorexia that user has been diagnosed with since puberty. Experts may include community experts. Community experts may include individuals in user's community who may provide encouragement, support, mentorship, guidance, and/or services to a user in response to user's desired behavior modification. Community may include a group of people having a shared characteristic. Shared characteristic may include individuals with a shared religious view, individuals with a shared political view, individuals who participate in a shared activity such as an organized sport, dinner club, knitting circle, book club, and the like. Community experts may include individuals who have a shared characteristic with user. For example, a community expert such as an individual who belongs to user's tennis club may provide support for user with a behavior modification to become more physically fit. In yet another non-limiting example, a community expert such as an individual who patriciates in a cooking class with user may provide encouragement for user with a behavior modification to cook more meals at home from scratch instead of relying on take out. Experts may include miscellaneous experts. Miscellaneous experts may include experts who may provide encouragement, support, mentorship, guidance, and/or services to a user in response to user's desired behavior modification pertaining to any other applicable industry. Experts may include informed advisors such as artificial intelligence informed advisors, spiritual professional informed advisors, nutrition professional informed advisors, fitness professional informed advisors, functional medicine informed advisors, friends and family informed advisors, electronic behavior coach informed advisors, and miscellaneous informed advisors.

With continued reference to FIG. 10, one or more database tables contained within expert database 532 may include expert demographics table 1000; expert demographics table 1000 may include background information about an expert such as name, address, phone number, email address, and any other identifying information that may be useful about an expert. One or more database tables contained within expert database 532 may include self-reported qualities table 1004; self-reported qualities table 1004 may contain any qualities that an expert may self-report. Qualities may include any of the qualities as described herein including both good and bad qualities. For example, an expert may self-report that expert is patient, slow to anger, and gentle while another expert may self-report an undesirable quality such as jealously. One or more database tables contained within expert database 532 may include peer-reviewed qualities table 1008; peer-reviewed qualities table 1008 may contain any qualities that a peer of expert may report about expert. Peer may include for example a friend, co-worker, family member, acquittance, and/or another user who expert helped in regard to a behavior modification. For example, a friend may provide information about certain qualities about an expert such that a particular expert is hopeful, dependable, and honest. One or more database tables contained within expert database 532 may include expert experience table 1012; expert experience table 1012 may include any information pertaining to a particular experience or behavior modification that an expert had experience with or overcame. For example, expert experience table 1012 may include information about an expert's struggle with alcohol addiction and different behavior modifications and experts that aided expert in overcoming expert's alcohol addiction. One or more database tables contained within expert database 532 may include expert credentials table 1016; expert credentials table 1016 may include any information pertaining to certain educational credentials or certificates or work credentials that an expert may possess. For example, expert credentials table may include information about a functional medicine doctor's training as a functional medicine doctor and any certificates functional medicine doctor may have completed such as training programs in addiction or hormonal health. In yet another non-limiting example, expert credentials table 1016 may include information about a therapist's license status or a health coach's certificate program. One or more database tables contained within expert database 532 may include expert values table 1020; expert values table 1020 may include information about an expert's personal values. Values may include for example, how an expert feels about certain values such as patience, kindness, truthfulness. Boastfulness. Rudeness, self-seeking and the like. One or more database tables contained within expert database 532 may include good fruits table 1024; good fruits table 1024 may include information about an expert's thoughts and experiences with good fruits. Good fruits may include positive mindsets and positive character traits, actions, and deeds such as love, joy, peace, self-control and the like. One or more database tables contained within expert database 532 may include bad fruits table 1028; bad fruits table 1028 may include information about an expert's thoughts and experiences with bad fruits. Bad fruits may include negative mindsets and negative character traits, actions and deeds such as sexual immorality, idolatry, debauchery, hatred, and jealousy.

Figure 11:
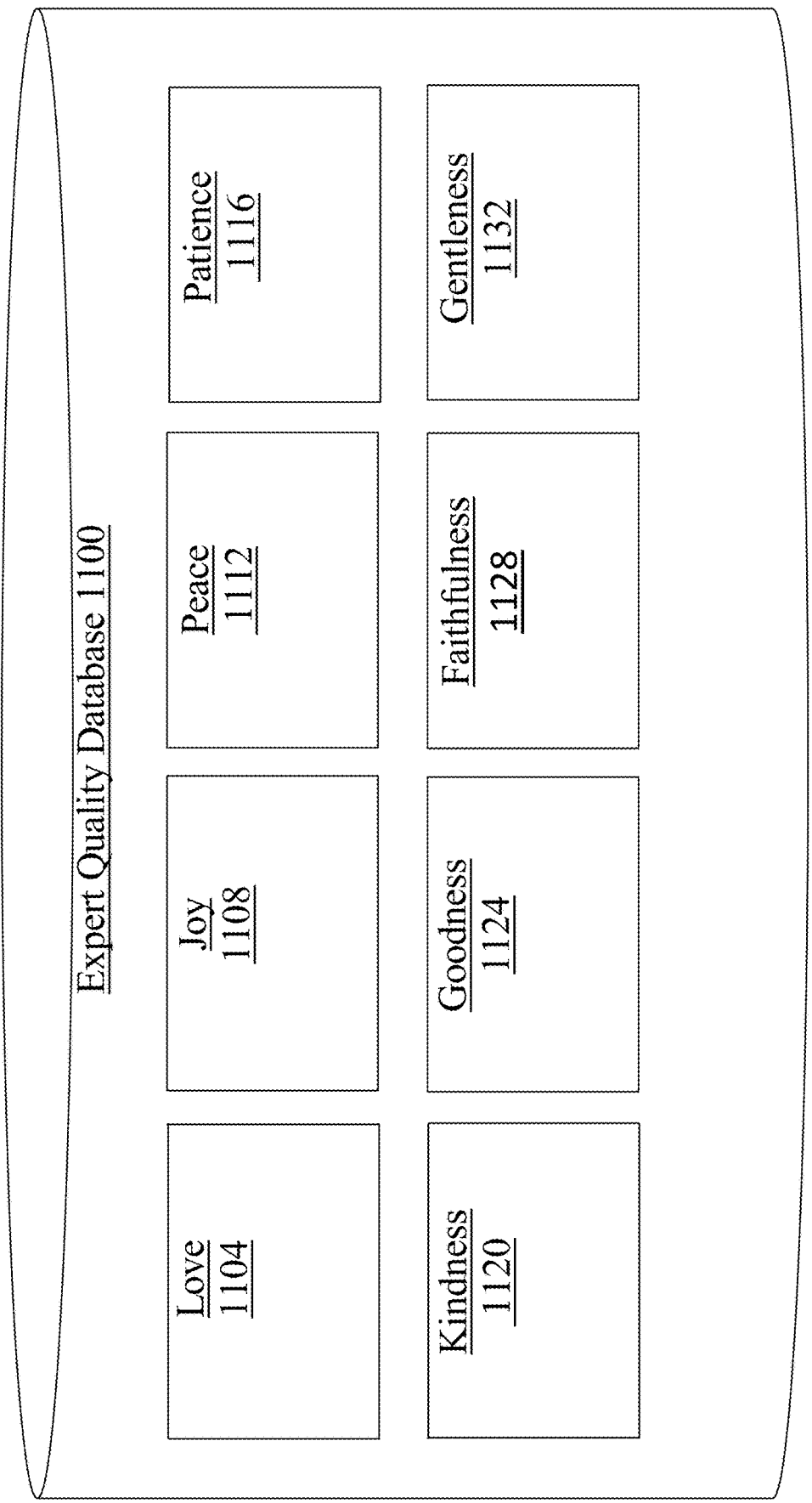
FIG. 11 is a block diagram illustrating an exemplary embodiment of an expert quality database; is a flow diagram illustrating an exemplary embodiment of method of behavioral pattern matching and language generation.

Referring now to FIG. 11, an exemplary embodiment of expert quality database 1100 is illustrated. Expert quality database 1100 may include any database or datastore suitable for language database as described above. Expert quality database 1100 may include one or more entries linking qualities associated with one or more experts. Linking may be performed by reference to historical data concerning experts such as previous encounters and/or interactions with specific experts. Qualities may include any of the experts as described herein. Qualities may be collected based on expert self-reported qualities and/or from peer reviewed information such as family members, friends, co-workers, and acquittances who may self-report a specific quality about an expert. Expert quality database 1100 may include one or more database tables containing information about a particular quality of an expert. One or more database tables contained within expert quality database 1100 may include love table 1104; love table 1104 may include information about an expert's commitment to the well-being of others. One or more database tables contained within expert quality database 1100 may include joy table 1108; joy table 1108 may include information about an expert's gladness not based on circumstances. One or more database tables contained within expert quality database 1100 may include peace table 1112; peace table 1112 may include information about an expert's lack of fear and sense of contentment. One or more database tables contained within expert quality database 1100 may include patience table 1116; patience table 1116 may include information about an expert's slowness to speak and slowness to anger. One or more database tables contained within expert quality database 1100 may include kindness table 1120; kindness table 1120 may include information about an expert's eagerness to put others at ease. One or more database tables contained within expert quality database 1100 may include goodness table 1124; goodness table 1124 may include information about an expert's generosity and openheartedness. One or more database tables contained within expert quality database 1100 may include faithfulness table 1128; faithfulness table 1128 may include information about an expert's dependability, loyalty, and trustworthiness. One or more database tables contained within expert quality database 1100 may include gentleness table 1132; gentleness table may include information about an expert's humbleness, calmness, and non-threatening abilities. In an embodiment, one or more database tables contained within expert quality database 1100 may include qualities that a user desires and/or seeks in an expert. In an embodiment, one or more database tables contained within expert quality database 1100 may include undesirable qualities of a user such as sexual immorality, lustfulness, idolatry, witchcraft, selfish ambitions, demons, debauchery, drunkenness, corruption, hatred, malice, deceit, jealousy, envy, anger, and greed. In an embodiment, qualities contained within expert quality database 1100 may include information such as how often an expert may exhibit any one particular quality. For example, qualities may be ranked such as never exhibiting, rarely exhibiting, sometimes exhibiting, frequently exhibiting, and always exhibiting.

Referring again to FIG. 5, expert list 520 may be generated based on classification of the at least a behavior modification. Classification as used herein includes pairing or grouping of behavior modifications as a function of some shared commonality. Behavior modifications may be grouped with certain health goals such as weight loss, food addiction, and physical inactivity which may generate an expert list 520 that contain an expert such as a nutritionist or fitness instructor. Behavior modifications grouped with certain alarm conditions such as depression, drug addiction, alcohol addiction may generate an expert list 520 that includes consultation with a functional medicine doctor. Expert list 520 may be generated based on groupings such as severity of behavior modification. For example, a user with a behavior modification such as a desire to drink less soda throughout the week may be linked to an expert list 520 that includes a support system of family, friends, and co-workers while a user with a behavior modification such as heroin addiction may be linked to an expert list 520 that includes trained medical professionals including functional medicine doctors, nurses, and addiction specialist. Classification of at least a behavior modification may include staging of a behavior modification. Staging may include dividing a behavior modification or goal into categories on a spectrum of behaviors and symptomology. For example, a user with a behavior modification such as attending church once each week may require experts such as friends and family members and fellow church-goers while a user with a behavior modification such as developing a Christian faith practice may require experts such as members of clergy, religious teachers, religious instructors, in addition to friends, family members, and fellow church-goers. . Expert list 520 may be generated by any of the methodologies as described in this disclosure.

Figure 12:
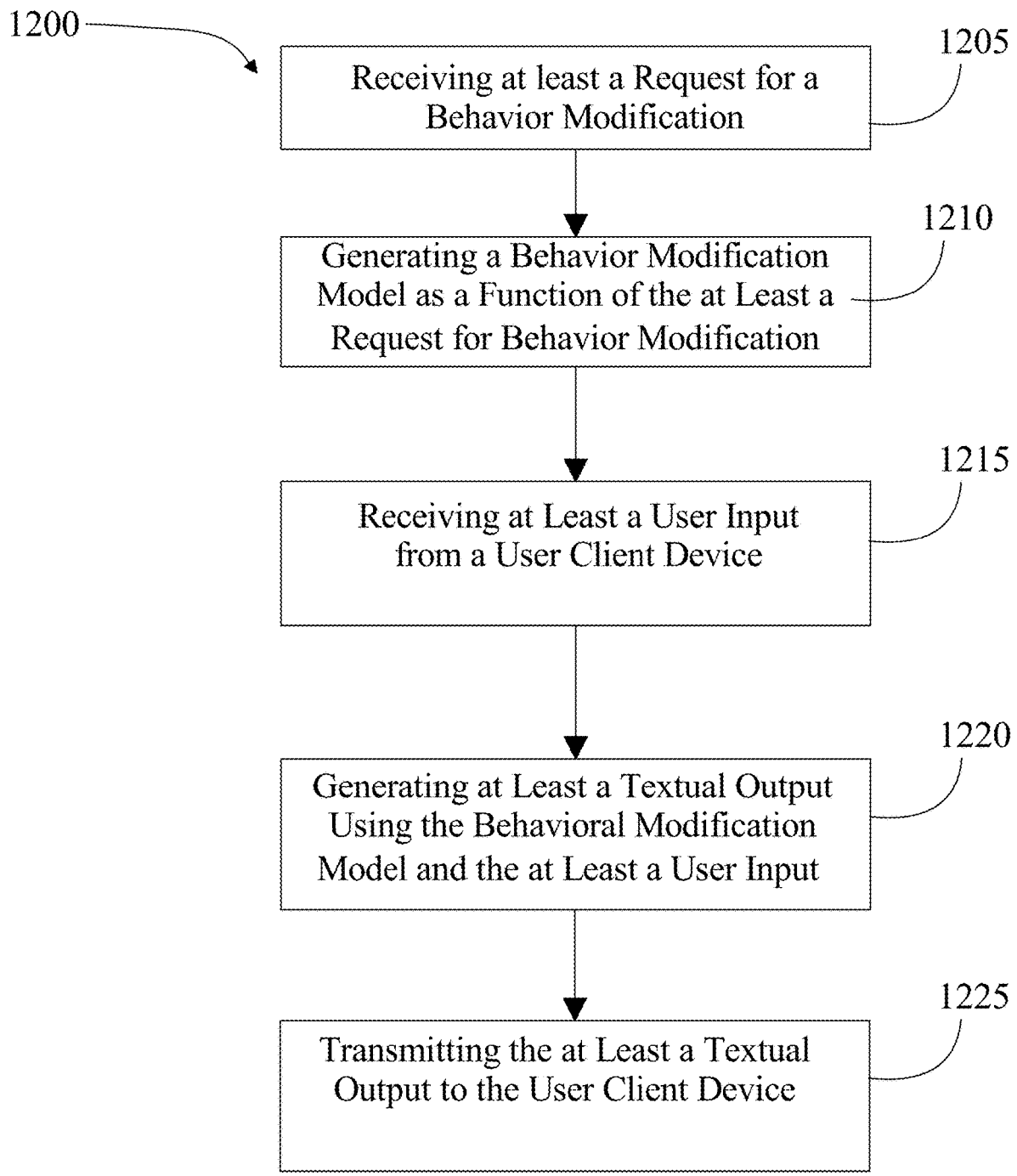

Turning now to FIG. 12, an exemplary embodiment of an artificial intelligence method 1200 of behavioral pattern matching and language generation is illustrated. At step 1205 at least a server 104 receives at least a request for a behavior modification; this may be implemented as described above in reference to FIGS. 1-11. At step 1210, at least a server 104 generates a behavior modification model as a function of the at least a request for behavior modification; this may be implemented as described above in reference to FIGS. 1-11. At step 1215 the at least a server receives at least a user input from a user client device; this may be implemented as described above in reference to FIGS. 1-11. As a non-limiting example, the at least a user input may include a textual input. As another non-limiting example, the at least user input may include at least an element of metadata.

Still referring to FIG. 12, at step 1220 at least a server generates at least a textual output using the behavior modification model and the at least a user input; this may be implemented as described above in reference to FIGS. 1-11. As a non-limiting example, generating the at least a textual output may include generating at least a query using the at least a user input and generating the at least a textual output as a function of the at least a query; this may include mapping, using a language processing module, the at least a user input to the at least a query. Generating the textual output may include determining that the at least a query includes a conversational language query and generating a conversational response using the conversational language query. Generating a conversational response may include retrieving at least a datum from a default response database using the conversational language query and generating the conversational response using the at least a datum. Generating a conversational response may include generating the at least a conversational response using a user communication learner. Generating at least a textual output may include determining that the at least a query includes an informational query and generating an informational response using the informational query. Generating an informational response may include retrieving at least a datum from the behavior modification model using the informational query and generating the informational response using the at least a datum.

At step 1225, and still referring to FIG. 12, at least a server transmits the at least a textual output to the user client device; this may be implemented as described above in reference to FIGS. 1-11.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
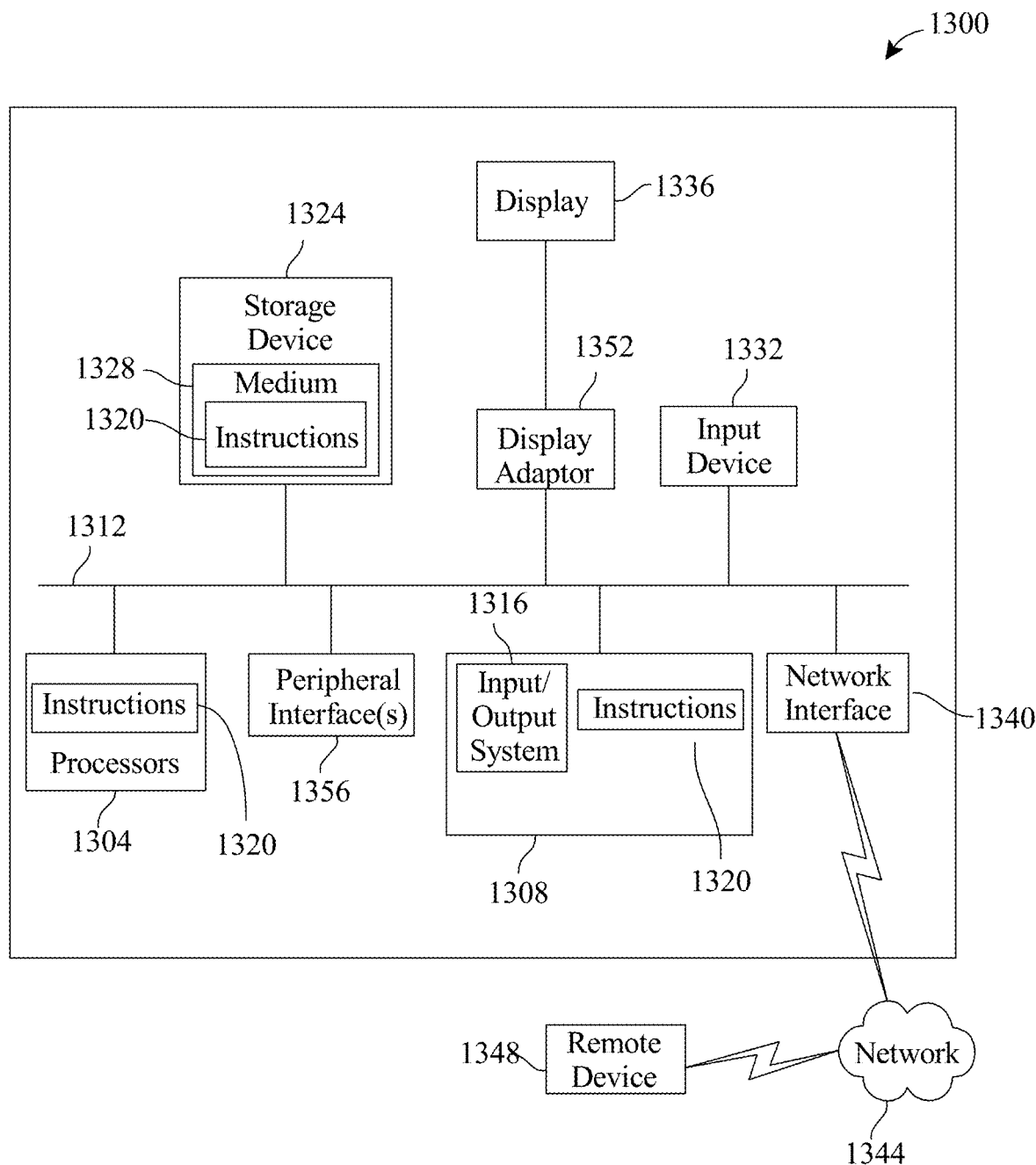
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An artificial intelligence system for providing a consultation for a user, the system comprising:
    a processor; and
    a memory containing instructions, the instructions configuring the processor to:
        extract one or more elements from a user input to detect a user query, wherein the user query comprises at least one of a conversational query and an informational query;
        detect a consultation event by matching one or more elements within the user query to a consultation action utilizing a consultation initiator which performs a machine learning operation on a machine-learning model, wherein performing the machine learning operation comprises:
            receiving a consultation training data set, wherein the consultation training data set comprises a plurality of word data and a plurality of phrase data correlated to categories of consultation events;
            training, iteratively, the machine-learning model using the consultation training data set and
            indicating the consultation event as a function of the trained machine-learning model and the word data and the phrase data;
        generate at least one textual output corresponding to at least one of the one or more elements within the user query, wherein the at least one textual output contains a category of the consultation event associated with an expert;
        store one or more of the at least one textual output, the user input, and the user query to a database;
        retrieve data corresponding to the stored one or more of the at least one textual output, the user input, and the user query from the database; and
        initiate the consultation by transmitting the retrieved data to the expert.

2. The artificial intelligence system of claim 1, wherein detecting the user query comprises applying a dependency parsing process to detect one or more syntactic elements within the user input.

3. The artificial intelligence system of claim 1, wherein the processor is further configured to store interactions between the user and other entities.

4. The artificial intelligence system of claim 1, wherein the user input and the at least one textual output are in a conversational language format.

5. The artificial intelligence system of claim 1, wherein at least one of the one or more elements of the user query are associated with a behavior.

6. The artificial intelligence system of claim 5, wherein the behavior is determined using metadata included in the user input.

7. The artificial intelligence system of claim 5, wherein the behavior is determined by correlating a plurality of different categories of the user input.

8. The artificial intelligence system of claim 1, wherein the expert is selected from an expert list based on one or more expert qualities associated with a behavior modification.

9. The artificial intelligence system of claim 1, wherein the expert is selected based on a user preference.

10. The artificial intelligence system of claim 1, wherein the textual output is generated based on a user history.

11. An artificial intelligence method for providing consultation for a user, the method comprising:
- extracting, by a processor, one or more elements from a user input to detect a user query, wherein the user query comprises at least one of a conversational query and an informational query;
- detecting, by the processor, a consultation event by matching one or more elements within the user query to a consultation action utilizing a consultation initiator which performs a machine learning operation on a machine-learning model,
  - wherein performing the machine learning operation comprises:
    - receiving a consultation training data set, wherein the consultation training data set comprises a plurality of word data and a plurality of phrase data correlated to categories of consultation events;
    - training, iteratively, the machine-learning model using the consultation training data set; and
    - indicating the consultation event as a function of the trained machine-learning model and the word data and the phrase data;
- generating, by the processor, at least one textual output corresponding to at least one of the one or more elements within the user query, wherein the at least one textual output contains a category of the consultation event associated with an expert;
- storing, by the processor, one or more of the at least one textual output, the user input, and the user query to a database;
- retrieving, by the processor, data corresponding to the stored one or more of the at least one textual output, the user input, and the user query from the database; and
- initiating, by the processor, the consultation by transmitting the retrieved data to the expert.

12. The method of claim 11, wherein detecting the user query comprises applying a dependency parsing process to detect one or more syntactic elements within the user input.

13. The method of claim 11, further comprising storing, by the processor, interactions between the user and other entities.

14. The method of claim 11, wherein the user input and the at least one textual output are in a conversational language format.

15. The method of claim 11, wherein at least one of the one or more elements of the user query are associated with a behavior.

16. The method of claim 15, further comprising determining, by the processor, the behavior using metadata included in the user input.

17. The method of claim 15, further comprising determining, by the processor, the behavior by correlating a plurality of different categories of the user input.

18. The method of claim 11, further comprising selecting, by the processor, the expert from an expert list based on one or more expert qualities associated with a behavior modification.

19. The method of claim 11, further comprising selecting, by the processor, the expert based on a user preference.

20. The method of claim 11, further comprising generating, by the processor, the textual output based on a user history.

* * * * *